(12) United States Patent
Summers et al.

(10) Patent No.: US 7,183,300 B2
(45) Date of Patent: Feb. 27, 2007

(54) INHIBITORS OF HIV-1 CAPSID FORMATION: SUBSTITUTED ARYL AMINOMETHYL THIAZOLE UREAS AND ANALOGUES THEREOF

(76) Inventors: Michael F. Summers, 2632 N. Rogers Ave., Ellicott City, MD (US) 21043; Atul Agarwal, 75 Nicholas Ct., Hamden, CT (US) 06518; Xi Chen, 17 Blueberry Hill Reserve, Killingworth, CT (US) 06419; Milind Deshpande, 44 Field Brook Rd., Madison, CT (US) 06443

( * ) Notice: Subject to any disclaimer, the term of this patent is extended or adjusted under 35 U.S.C. 154(b) by 0 days.

(21) Appl. No.: 11/271,437

(22) Filed: Nov. 10, 2005

(65) Prior Publication Data

US 2006/0100232 A1    May 11, 2006

Related U.S. Application Data

(60) Provisional application No. 60/626,902, filed on Nov. 11, 2004.

(51) Int. Cl.
| | |
|---|---|
| A61K 31/4245 | (2006.01) |
| A61K 31/426 | (2006.01) |
| A61K 31/341 | (2006.01) |
| C07D 271/08 | (2006.01) |
| C07D 277/48 | (2006.01) |
| C07D 307/54 | (2006.01) |

(52) U.S. Cl. ............... 514/364; 514/377; 514/461; 548/125; 548/196; 549/473

(58) Field of Classification Search ............ 564/32; 548/196, 125; 514/364, 377, 461; 549/473
See application file for complete search history.

(56) References Cited

U.S. PATENT DOCUMENTS

| | | | |
|---|---|---|---|
| 5,162,360 A | 11/1992 | Creswell et al. | |
| 5,424,431 A | 6/1995 | Ohta et al. | |
| 6,649,641 B2 | 11/2003 | Behrens et al. | |
| 6,762,318 B2 | 7/2004 | Kodra et al. | |
| 6,881,746 B2 | 4/2005 | Lau et al. | |

FOREIGN PATENT DOCUMENTS

WO    WO 2005/092865 A1    10/2005

OTHER PUBLICATIONS

Chaimbault, et al. "Synthesis, Antitumour and Anti-HIV Screening of Oxazolidines and Oxazolidinones Derivatives" Pharm. Pharmacol. Commun. 1999, vol. 5, pp. 211-215.*

Chun Tang, et al., "Antiviral Inhibition of the HIV-1 Capsid Protein," J. Mol. Biol. 32: 1013-1020 (2003).

Chaimbault, C. et al., "Synthesis, Antitumour and Anti-HIV Screening of Oxazolidines and Oxazolidinones Derivatives," Pharm. Pharmacol. Commun. (1999) 5: 211-215.

Database Beilstein [online], Beilstein Institut Zur Foederung Der Chemischen Wissenschaften, DE; Database Accession No. 3008250, 3005712, 301178 (BRN) abstract & Gehlen, H. et al.: Journal Fuer Praktische Chemie, Wiley, Weinheim, DE, (1968) 38: 107-112.

International Search Report for International Application No. PCT/US2005/041358, mailed Jul. 6, 2006.

* cited by examiner

Primary Examiner—Joseph K. McKane
Assistant Examiner—Joseph R. Kosack
(74) Attorney, Agent, or Firm—Cantor Colburn LLP

(57) ABSTRACT

Substituted aryl aminomethyl thiazole ureas and analogues thereof that act as inhibitors of viral capsid formation, including HIV capsid formation, are provided here. Generally the virus capsid formation inhibitors described herein are compounds of Formula I

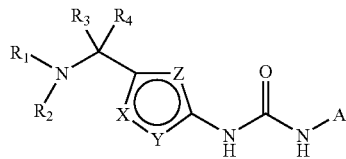

where A is a group of formula (a) or (b)

Formula I

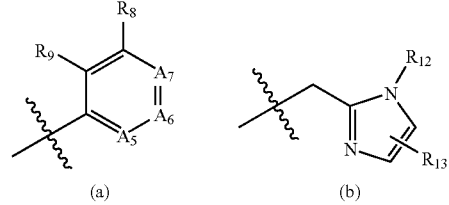

wherein the variables A, $R_1$, $R_2$, $R_3$, $R_4$, X, Y, Z, $A_5$, $A_6$, $A_7$, $R_8$, $R_9$, $R_{12}$, and $R_{13}$ are defined herein. Pharmaceutical compositions comprising such compounds and methods of treating animals infected with a virus having a capsid protein are provided herein. Methods of using such compounds to treat human patients infected with an HIV virus and reducing the mortality of AIDS are also provided herein.

20 Claims, 2 Drawing Sheets

Chemical shift changes as a function of added CAP-1, used to determine $K_D$.

INHIBITORS OF HIV-1 CAPSID FORMATION: SUBSTITUTED ARYL AMINOMETHYL THIAZOLE UREAS AND ANALOGUES THEREOF

CROSS REFERENCE TO RELATED APPLICATIONS

This application claims priority to U.S. Provisional Application No. 60/626,902 filed Nov. 11, 2004 which is hereby incorporated by reference in its entirety.

FIELD OF THE INVENTION

Substituted aryl aminomethyl thiazole ureas and analogues thereof thought to act as inhibitors of viral capsid formation are provided here. Certain of these compounds act as highly active inhibitors of HIV, including HIV-1, capsid formation. Pharmaceutical compositions comprising such compounds and methods of treating patients infected with an encapsulated virus, especially HIV, and reducing the mortality of viral diseases, such as AIDS, are also provided herein.

BACKGROUND

Retroviruses are viruses that contain single-stranded RNA particles enveloped in a protein capsid. The family retrovirus family consists of three groups: the spumaviruses such as the human foamy virus; the lentiviruses, such as the human immunodeficiency virus types 1 and 2, as well as visna virus of sheep; and the oncoviruses.

The retrovirus particle is composed of two identical RNA molecules. Each genome is a positive sense, single-stranded RNA molecule, which is capped at the 5' end and polyadenylated at the 3' tail. The prototype C-type oncoviral RNA genome contains three open reading frames call gag, pol and env, bounded by regions that contain signals essential for expression of the viral genes. The gag region encodes the structural proteins of the viral capsid. The pol region encodes a viral proteinase as well as the proteins for genome processing, including reverse transcriptase, ribonuclease H and endonuclease enzymatic activities. The env region specifies the glycoproteins of the viral envelope. In addition to these three open reading frames, the more complex genomes of the lentiviruses and the spumaviruses carry additional open reading frames, which encode regulatory proteins involved in the control of genome expression.

AIDS is a retroviral disease caused by HIV, a non-transforming human retrovirus belonging to the lentivirus family. Two genetically different but related forms of HIV, called HIV-1 and HIV-2, have been isolated from patients with AIDS. HIV-1 is the most common type associated with AIDS in the United States, Europe, and Central Africa, whereas HIV-2 causes a similar disease principally in West Africa.

Like most retroviruses, the HIV-1 virion is spherical and contains an electron-dense, cone shaped core surrounded by a lipid envelope derived from the host cell membrane. The virus core contains (1) the major capsid protein p24 (CA), (2) nucleocapsid protein p7/ p9, (3) two copies of genomic RNA, and (4) the three viral enzymes (protease (PR), reverse transcriptase (RT), and integrase). A matrix protein called p17, which lies underneath the virion envelope, surrounds the viral core. Studding the viral envelope are two viral glycoproteins, gp 120 and gp 41, which are critical for HIV infection of cells.

As with other retroviruses, the HIV proviral genome contains the gag, pol, and env genes, which code for various viral proteins. The products of the gag and pol genes are translated initially into large precursor proteins that must be cleaved by the viral protease to yield the mature proteins.

The CA is initially synthesized as a domain within a 55 kDa Gag precursor polyprotein. Approximately 4,000 copies of Gag assemble at the plasma membrane and bud to form an immature virus particle. Subsequent to budding, the CA is liberated by proteolytic cleavage of Gag, which triggers a conformational change that promotes assembly of the capsid particle. Two copies of the viral genome and enzymes essential for infectivity become encapsidated in the central, cone shaped capsid of the mature virion. The CA domain of Gag is also responsible for packaging about 200 copies of the host protein, CypA, which is a prolyl isomerase and a chaperone protein that is essential for HIV-1 infectivity. Although the precise function of CypA is not known, it is suspected that the protein facilitates disassembly of the capsid core during infectivity.

Several recent studies have shown that proper capsid assembly is critical for viral infectivity. Mutations in CA that inhibit assembly are lethal and mutations that alter capsid stability and severely attenuate replication making the CA an attractive potential antiviral target. Although antiviral agents have been developed that bind to the capsid protein of picornaviruses and suppress infectivity by inhibiting disassembly of the capsid shell, inhibitors of HIV capsid assembly or disassembly have not yet been developed as drugs.

Currently available drugs for the treatment of HIV infection target the reverse transcriptase (RT) and HIV-1 protease (PR) enzymes, two of fifteen proteins encoded by the viral genome. These drugs are marginally effective when administered independently due to the rapid emergence of resistant strains that are selected under conditions of incomplete viral suppression. Sustained reductions in viral load can be achieved when RT and PR inhibitors are used in appropriate combinations (highly affective anti-retroviral therapy, HAART). But inadequate suppression due to poor compliance, resistance, and interactions with other drugs or diet is a significant problem that limits the effectiveness of HAART therapy for many patients and can lead to the spread of drug-resistant strains.

AIDS is characterized by profound immunosuppression that leads to opportunistic infections, secondary neoplasms and neurologic manifestations. In spite of the availability of HAART therapy, the mortality and morbidities associated with AIDS remain significant and unresolved by current therapies. New therapeutic compounds and methods are needed that could reduce or ameliorate the adverse events and improve the clinical outcome of AIDS, including, for example, reducing mortality and improving the quality of life of those suffering from the disease.

SUMMARY OF INVENTION

Inhibitors of viral capsid formation, such as the capsids formed by retroviruses including HIV viruses, including the HIV-1 virus, are provided herein. Certain inhibitors provided herein bind to the apical cleft of viral capsid protein, which in the HIV-1 virus includes the C-terminal of helix 1, the N-terminals of helices 2 and 4, the C-terminal of helix 3, and the C-terminal of helix 7. Inhibitors of viral capsid formation provided herein are generally substituted aryl aminomethyl thiazole ureas and analogues thereof of Formula I and pharmaceutically acceptable salts thereof.

Thus in a first aspect compounds and pharmaceutically acceptable salts of Formula I are provided herein.

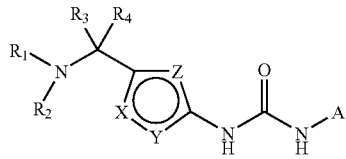

where A is a group of formula (a) or (b)

Formula I

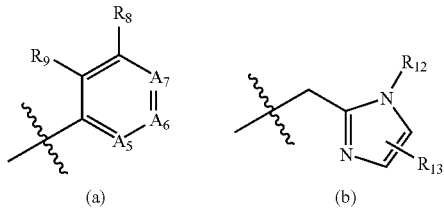

Wherein:

X, Y, and Z are each independently N, NR, S, O, or CR', wherein at least one of X, Y, and Z is N, NR, S, or O.

R is hydrogen, $C_1$–$C_4$alkyl, or $C_2$–$C_4$alkenyl.

Each R' is independently hydrogen, halogen, hydroxy, $C_1$–$C_4$alkyl, $C_2$–$C_4$alkenyl, $C_2$–$C_4$alkynyl, $C_1$–$C_4$alkoxy, mono- or di-($C_1$–$C_4$alkyl)amino, $C_2$–$C_4$alkanoyl, $C_2$–$C_4$alkoxycarbonyl, $C_1$–$C_2$haloalkyl, or $C_1$–$C_2$haloalkoxy.

When X is NR or CR', X may be taken together with $R_2$ to form a 5 to 7 membered heterocyclic ring, which is partially unsaturated or aromatic, and is substituted with 0 to 3 substituents independently chosen from halogen, hydroxy, cyano, amino, oxo, $C_1$–$C_4$alkyl, $C_1$–$C_4$alkoxy, mono- and di-($C_1$–$C_4$alkyl)amino, $C_1$–$C_2$haloalkyl, and $C_1$–$C_2$haloalkoxy.

$R_1$ is hydrogen, or $R_1$ is $C_1$–$C_6$alkyl, $C_2$–$C_6$alkenyl, $C_2$–$C_6$alkenyl, ($C_3$–$C_7$cycloalkyl)$C_0$–$C_2$alkyl, (heterocycloalkyl)$C_0$–$C_2$alkyl, or (phenyl)$C_0$–$C_2$alkyl, each of which is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

$R_2$ is hydrogen, or $R_2$ is $C_1$–$C_6$alkyl, $C_2$–$C_6$alkenyl, $C_2$–$C_6$alkenyl, ($C_3$–$C_7$cycloalkyl)$C_0$–$C_2$alkyl, (heterocycloalkyl)$C_0$–$C_2$alkyl, or (phenyl)$C_0$–$C_2$alkyl, each of which is substituted with 0 to 3 substituents independently chosen from halogen, hydroxy, cyano, amino, nitro, oxo, —(C=O) NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

Or $R_1$ and $R_2$ are taken together to form a monocyclic or bicyclic heterocycle, which heterocycle is saturated, partially unsaturated, or aromatic, and is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

Or $R_2$ may be taken together with X.

$R_3$ and $R_4$ are independently hydrogen, halogen, hydroxy, $C_1$–$C_4$alkyl, $C_1$–$C_4$alkoxy, mono- or di-($C_1$–$C_4$alkyl) amino, $C_1$–$C_2$haloalkyl, or $C_1$–$C_2$haloalkoxy.

$A_5$ is N or $CR_5$; $A_6$ is N or $CR_6$; and $A_7$ is N or $CR_7$; where not more than one of $A_5$, $A_6$, and $A_7$, is Nitrogen.

$R_5$ is hydrogen, halogen, hydroxy, cyano, amino, straight chain $C_1$–$C_4$alkyl, straight chain $C_1$–$C_4$alkoxy, mono- or di-($C_1$–$C_4$alkyl)amino, $C_1$–$C_2$haloalkyl, or $C_1$–$C_{C2}$haloalkoxy.

Or, $R_5$ is joined with $R_6$ to form a phenyl ring or a 5- or 6-membered heteroaryl ring having 1 or 2 heteroatoms independently chosen from N, O, and S, each of which is substituted with 0 to 3 substituents independently chosen from halogen, hydroxy, cyano, amino, nitro, —(C=O) NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

$R_6$ and $R_7$ are independently (i) hydrogen, halogen, hydroxy, cyano, amino, or nitro; or (ii) $C_1$–$C_6$alkyl, $C_2$–$C_6$alkenyl, $C_2$–$C_6$alkynyl, $C_1$–$C_6$alkoxy, $C_2$–$C_6$alkanoyl, ($C_3$–$C_7$cycloalkyl) $C_0$–$C_2$alkyl, (heterocycloalkyl)$C_0$–$C_2$alkyl, (phenyl) $C_0$–$C_{C2}$alkyl, mono- or di-($C_1$–$C_6$alkyl)amino, $C_1$–$C_2$haloalkyl, or $C_1$–$C_2$haloalkoxy; each of which is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy, or (iii) a 5 membered heteroaryl group containing 1 or 2 heteroatoms independently chosen from N, S, and O.

Or, $R_5$ is joined with $R_6$.

Or, $R_6$ and $R_7$ are joined to form a phenyl ring or a 5- or 6-membered heteroaryl ring having from 1 to 3 heteroatoms independently chosen from N, O, and S, each of which is substituted with 0 to 3 substituents independently chosen from halogen, hydroxy, cyano, amino, nitro, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

$R_8$ and $R_9$ are independently hydrogen, halogen, hydroxy, cyano, amino, straight chain $C_1$–$C_4$alkyl, straight chain $C_1$–$C_4$alkoxy, mono- or di-($C_1$–$C_4$alkyl)amino, $C_1$–$C_{C2}$haloalkyl, or $C_1$–$C_2$haloalkoxy.

$R_{12}$ is hydrogen, $C_1$–$C_6$alkyl, or ($C_3$–$C_7$cycloalkyl) $C_0$–$C_4$alkyl.

$R_{13}$ is 0 to 2 substituents independently chosen from halogen, methyl, ethyl, methoxy, ethoxy, trifluoromethyl, and trifluoromethoxy.

A pharmaceutical composition, comprising a compound or salt of Formula I, in combination with at least one pharmaceutically acceptable carrier or excipient is also provided herein. The pharmaceutical composition may be formulated as an injectable fluid, an aerosol, a cream, an oral liquid, a tablet, a gel, a pill, a capsule, a syrup, or a transdermal patch, or in another pharmaceutically efficacious form.

A method for inhibiting viral capsid formation in cells, comprising contacting cells infected with a virus with a compound or salt of Formula I, in an amount sufficient to detectably inhibit viral capsid formation in vitro, and thereby inhibiting viral capsid formation in the cells is provided herein. The virus may be any virus having a capsid protein, but in certain embodiments is a retrovirus, a family of viruses that includes HIV viruses, such as the HIV-1 virus. A method of inhibiting viral capsid formation by contacting cells infected with a virus having a capsid protein with a compound or salt of Formula I, in an amount sufficient to detectably bind to the capsid protein apical cleft, and thereby inhibiting viral capsid formation is also provided herein.

Within certain embodiments provided herein the cells infected with a virus having a capsid protein are present in a human.

A method of treating an animal infected with a virus having a capsid protein comprising administering a therapeutically effective amount of a compound of salt of Formula I to the animal is provided herein. In certain embodiments the virus having a capsid protein is an HIV virus, such as the HIV-1 virus. A method of reducing mortality of HIV-1 infection or AIDS comprising administering a therapeutically effective amount of a compound of Formula I to a human suffering from HIV-1 infection/AIDS is also provided herein. In certain embodiments provided herein the compound or salt of Formula I binds to the apical cleft of viral capsid protein.

DETAILED DESCRIPTION

Figure 1:
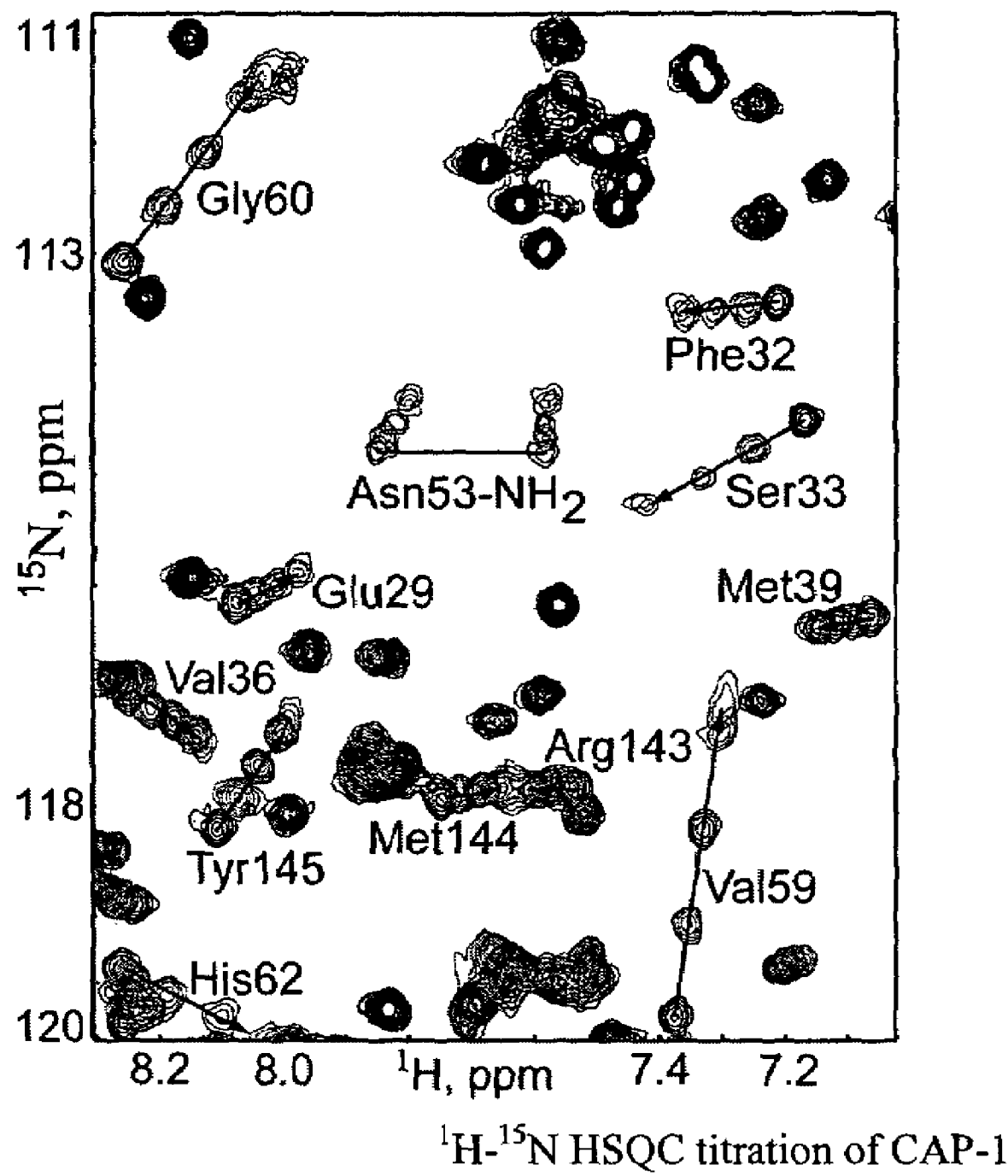
FIG. 1. Representative 1H-15N HSQC NMR data obtained upon titration of the capsid with CAP-1.
Figure 2:
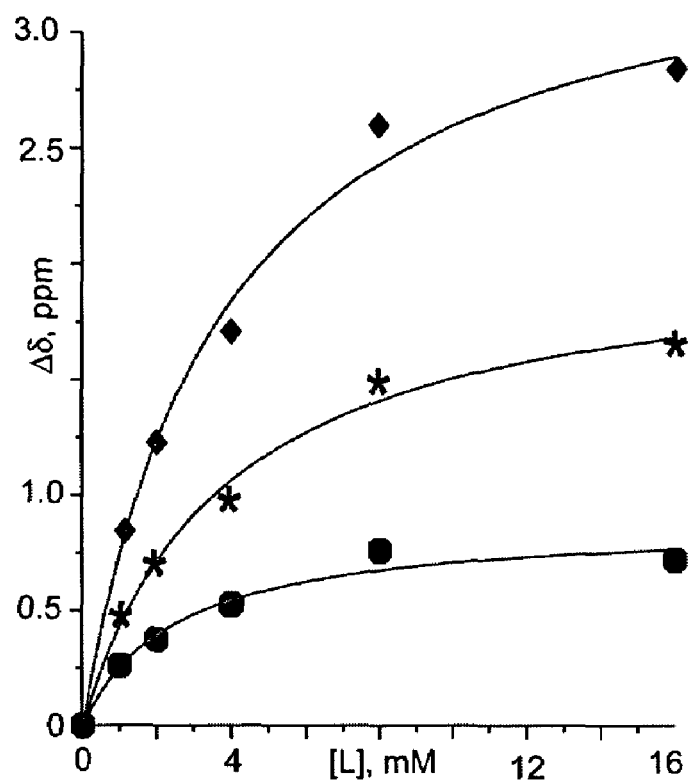
FIG. 2. Chemical shift changes as a function of added CAP-1, used to determine $K_D$.

As noted above, the present invention provides substituted aryl aminomethyl thiazole ureas and analogues thereof of Formula I. Such compounds may be used in vitro or in vivo, to inhibit viral capsid formation in viruses having a viral capsid such as retroviruses, which include the HIV virus, and particularly the HIV-1 virus, and possess additional uses, as discussed in further detail below.

TERMINOLOGY

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included unless otherwise specified. Where a compound exists in various tautomeric forms, a recited compound is not limited to any one specific tautomer, but rather is intended to encompass all tautomeric forms. Compound descriptions are intended to encompass compounds with all possible isotopes of atoms occurring in the compounds. Isotopes are those atoms having the same atomic number but different mass numbers. By way of general example, and without limitation, isotopes of hydrogen include tritium and deuterium and isotopes of carbon include $^{11}C$, $^{13}C$, and $^{14}C$. Certain compounds are described herein using a general formula that includes variables (e.g., $R_1$, $R_2$, $R_3$). Unless otherwise specified, each variable within such a formula is defined independently of any other variable, and any variable that occurs more than one time in a formula is defined independently at each occurrence. In general, the variables (e.g. $R_1$, $R_2$, $R_3$) may have any definition described herein that results in a stable compound.

The terms "substituted aryl aminomethyl thiazole ureas and analogues thereof" as used herein, encompass all compounds that satisfy Formula I, including any enantiomers, racemates, and stereoisomers, as well as all pharmaceutically acceptable salts of such compounds.

A "pharmaceutically acceptable salt" of the compounds recited herein is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

It will be apparent that each compound of Formula I may, but need not, be formulated as a hydrate, solvate or noncovalent complex. In addition, the various crystal forms and polymorphs are within the scope of the present invention. Also provided herein are prodrugs of the compounds of Formula I. A "prodrug" is a compound that may not fully satisfy the structural requirements of the compounds provided herein, but is modified in vivo, following administration to a patient, to produce a compound of Formula I, or other formula provided herein. For example, a prodrug may be an acylated derivative of a compound as provided herein. Prodrugs include compounds wherein hydroxy, amine or sulfhydryl groups are bonded to any group that, when administered to a subject, cleaves to form a free hydroxy, amino, or sulfhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved to the parent compounds.

As used herein, the term "alkyl" refers to a straight chain or branched chain saturated aliphatic hydrocarbon having the indicated number of carbon atoms. For example a $C_1$–$C_6$alkyl group has from 1 to about 6 carbon atoms. Alkyl groups include groups having 1 to 6 carbon atoms ($C_1$–$C_6$alkyl) and from 1 to 4 carbon atoms ($C_1$–$C_4$alkyl), and from 1 to 2 carbon atoms ($C_1$–$C_2$alkyl) such as methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. "$C_0$–$C_n$alkyl" refers to a single covalent bond ($C_0$) or an alkyl group having from 1 to about n carbon atoms. For example "$C_0$–$C_6$alkyl" refers to a single covalent bond or a $C_1$–$C_6$alkyl group. An alkyl group may be bonded to an atom within a molecule of interest via any chemically suitable portion.

Similarly, "alkenyl" refers to straight or branched chain hydrocarbon groups, in which at least one unsaturated carbon-carbon double bond is present. Alkenyl groups include $C_2$–$C_6$alkenyl, and $C_2$–$C_4$alkenyl groups, which have from 2 to 6, or 2 to 4 carbon atoms, respectively, such as ethenyl, allyl, or isopropenyl.

"Alkynyl" refers to straight or branched chain alkyne groups, which have one or more unsaturated carbon-carbon bonds, at least one of which is a triple bond. Alkynyl groups include $C_2$–$C_6$alkynyl, and $C_2$–$C_4$alkynyl groups, which have from 2 to 6, or 2 to 4 carbon atoms, respectively. Alkenyl and alkynyl groups may be straight or branched chain.

By "alkoxy," as used herein, is meant an alkyl group as described above attached via an oxygen bridge. Alkoxy groups include $C_1$–$C_6$alkoxy, and $C_1$–$C_4$alkoxy groups, which have from 1 to 6, or 1 to 4 carbon atoms, respectively. Alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy.

As used herein the term "alkoxycarbonyl" indicates an alkoxy group, as defined above, having the indicated number of carbon atoms, attached through a keto (—(C=O)—) bridge. The alkoxy moiety of the alkoxycarbonyl group has the indicated number of carbon atoms, the carbon of the keto bridge is not included in this number. For example, $C_3$alkoxycarbonyl indicates groups of the formula $CH_3$($CH_2$)$_2$—O—(C=O)— or ($CH_3$)$_2$(CH)—O—(C=O)—.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3$(C=O)—.

"Alkylamino" refers to a secondary or tertiary amine having the general structure —NH(alkyl) or —N(alkyl)(alkyl), wherein each alkyl may be the same or different. Such groups include, for example, mono- and/or di-($C_1$–$C_6$alkyl)amino groups, in which each alkyl is straight, branched or cyclic and may be the same or different and contains the indicated number of carbon atoms, for example from 1 to 6 carbon atoms or from 1 to 4 carbon atoms.

A "cycloalkyl" group is a fully saturated cyclic group containing carbon atoms as ring members. Cycloalkyl group included 3- to 7-membered cycloalkyl groups having a single saturated ring, e.g. cyclopropyl, cyclopentyl, and cyclohexyl. A "(cycloalkyl)$C_0$–$C_n$alkyl" is a cycloalkyl group linked via a single covalent bond or a $C_1$–$C_n$alkyl group, e.g. a $C_1$–$C_4$alkyl group.

The term "halogen" refers to fluorine, chlorine, bromine and iodine.

A "haloalkyl" is a branched or straight-chain alkyl group, substituted with 1 or more halogen atoms (e.g., "$C_1$–$C_2$haloalkyl" groups have from 1 to 2 carbon atoms). Examples of haloalkyl groups include, but are not limited to, mono-, di-, or tri-fluoromethyl; mono-, di-, or tri-chloromethyl; mono-, di-, tri-, tetra-, or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl.

"Haloalkoxy" indicates a haloalkyl group as defined above attached through an oxygen bridge. "$C_1$–$C_2$haloalkoxy" groups have from 1 to 2 carbon atoms.

A dash ("-") that is not between two letters or symbols is used to indicate a point of attachment for a substituent. For example, —$CONH_2$ is attached through the carbon atom.

A "heteroatom," as used herein, is oxygen, sulfur, or nitrogen.

A "monocyclic or bicyclic heterocyclic group" has 1 to 2 fused, pendant, or spiro rings, at least one of which is a heterocyclic ring (i.e., one or more ring atoms is a heteroatom, with the remaining ring atoms being carbon). Typically, a heterocyclic ring comprises 1, 2, 3, or 4 heteroatoms; within certain embodiments each heterocyclic ring has 1 or 2 heteroatoms per ring. Each heterocyclic ring generally contains from 3 to 8 ring members (rings having from 4 or 5 to 7 ring members are recited in certain embodiments) and bicyclic heterocycles typically comprise two fused, pendant, or spiro rings typically and contain at total of about 9 to about 14 ring members. Certain heterocycles comprise a sulfur atom as a ring member; in certain embodiments the sulfur atom is oxidized to SO or $SO_2$. Unless otherwise specified, a heterocycle may be a heterocycloalkyl group (i.e., each ring is saturated), a partially unsaturated group, or a heteroaryl group (i.e., at least one ring within the group is aromatic). A heterocyclic group may generally be linked via any ring or substituent atom, provided that a stable compound results. N-linked heterocyclic groups are linked via a component nitrogen atom. Certain heterocyclic groups are 4- to 7-membered or 5- to 7-membered groups that are optionally substituted. 4-to 7-membered heterocycloalkyl groups include, for example, piperidinyl, piperazinyl, pyrrolidinyl, azepanyl, morpholino, thiomorpholino, and 1,1-dioxo-thiomorpholin-4-yl. Such groups may be substituted as indicated. Representative aromatic heterocycles are thienyl, pyridyl, pyrimidyl, imidazolyl, and thiazolyl.

In certain embodiments preferred heterocycles are 5- to 7-membered heterocycle having a single saturated, partially unsaturated or aromatic heterocyclic ring with 5 to 7 ring members, 1 or 2 ring members independently chosen from N, O, and S, with remaining ring members being carbon.

Within certain embodiments a heterocyclic group may be attached via an indicated linker group. For example (heterocycloalkyl)alkyl substituents are present in some embodiments described herein. In each case the heterocylcic group carries the definition set forth above and is covalently bound to the indicated linker group, which carries the definition set forth above.

As used herein, "heteroaryl" indicates a 5- to 7-membered monocyclic aromatic ring which contains from 1 to 3, or preferably from 1 to 2, heteroatoms chosen from N, O, and S, with remaining ring atoms being carbon or a bicyclic or tricyclic system containing at least one 5- to 7-membered aromatic ring which contains from 1 to 3, or preferably from 1 to 2, heteroatoms independently chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

A "heterocycloalkyl" group is a heterocycle as described above, which is fully saturated. In certain embodiments preferred heterocycloalkyl groups are 5- to 7-membered heterocycloalkyl groups having a single saturated ring with 5 to 7 ring members, 1 or 2 ring members independently chosen from N, O, and S, with remaining ring members being carbon. A "(heterocycloalkyl)$C_0$–$C_n$alkyl" is a heterocycloalkyl group linked via a single covalent bond or $C_1$–$C_n$alkyl group, e.g. a $C_1$–$C_4$alkyl group.

A "substituent," as used herein, refers to a molecular moiety that is covalently bonded to an atom within a molecule of interest. For example, a ring substituent may be a moiety such as a halogen, alkyl group, haloalkyl group or other group discussed herein that is covalently bonded to an atom (preferably a carbon or nitrogen atom) that is a ring member. Substituents or aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized and tested for biological activity) results from the substitution.

The term "effective amount" means an amount effective, when administered to a human or non-human patient, to provide any therapeutic benefit such as an amelioration of symptoms, e.g., an amount effective to decrease the symptoms of a viral infection, and preferably an amount sufficient to reduce the symptoms of an HBV or HIV infection. In certain circumstances a patient suffering from a viral infection may not present symptoms of being infected. Thus a therapeutically effective amount of a compound is also an amount sufficient to provide a positive effect on any indicia of disease, e.g. an amount sufficient to prevent a significant increase or significantly reduce the detectable level of virus or viral antibodies in the patient's blood, serum, or tissues. A significant increase or reduction in the detectable level of virus or viral antibodies is any detectable change that is statistically significant in a standard parametric test of statistical significance such as Student's T-test, where $p<0.05$.

A "patient" is any human or non-human animal in need of medical treatment. Medical treatment can include treatment of an existing condition, such as a disease or disorder, or prophylactic or preventative treatment. In some embodiments the patient is a human patient.

INHIBITORS OF HIV-1 CAPSID FORMATION

The CA of mature HIV-1 contains a known N-terminal β-hairpin that is essential for formation of the capsid core particle. The residues of this hairpin are highly conserves and it is likely that all other retroviruses except the spumaviruses contain a similar N-terminal β-hairpin. Mutagenesis studies of the β-hairpin indicate that it is essential for HIV-1 capsid core particles and that that it probably functions by participating directly in intermolecular CA-CA interactions. Thus, the β-hairpin was originally chosen as a target for designed capsid formation inhibitors.

NMR studies have revealed an additional binding site (apical cleft) in the N-terminal domain of CA. This apical cleft includes the C-terminal of helix 1, the N-terminals of helices 2 and 4, the C-terminal of helix 3, and the C-terminal of helix 7. Without wishing to be bound by any particular theory it is believed that the anti-viral properties of compounds and salts of Formula I are due to interactions of these compounds with the apical cleft of the N-terminal domain of CA. Unlike the β-hairpin pocket, the apical cleft is present on both the mature and immature forms of the N-terminal domain of CA. Compounds that bind to this apical cleft inhibit capsid assembly and have antiviral properties. Residues of CA with backbone amide signals that are most significantly perturbed by binding of inhibitors to the apical cleft are either strictly conserved (Glu 35, Val 36, Val 59, Gly 60, His 62, Gln 63, Ala 65, Tyr 145) or rarely and conservatively substituted (number of occurrences in parentheses: E29D (2) K30R (1), A31G (16,), A31N (1), F32L (1), SeeN (13), G61E (1), M144T (1)) among the 93 genome sequences in the HIV Sequence Compendium. Most of the conserved residues are exposed on the surface of the N-terminal domain suggesting a possible macromolecular interactive function. Residues of the apical cleft of the N-terminal domain participate in an intermolecular interface upon in vitro capsid formation. Inhibitor compounds can function mechanistically by inhibiting intermolecular CA-CA interactions necessary for proper capsid assembly.

Residues Trp 23 and Val 59 exhibit significant chemical shift changes upon inhibitor ligand binding despite the fact that they are buried between helices 1, 2 and 3 of the CA monomer. It is, therefore, likely that the assembly inhibitors alter the local structure of the capsid protein and may thereby either competitively inhibit CA-CA interactions or promote the formation of a structurally distorted capsid shell.

Inhibition of capsid assembly does not require ligands with exceptionally high affinity for CA. This is likely due to the high local concentration of Gag molecules in assembled virions (14 mM), which favors binding by ligands with even modest affinities, e.g., N-(3-chloro-4-methylphenyl)-N'-[2-[([5-[(dimethylamino)-methyl]-2-furyl]-methyl)-sulfanyl]ethyl]urea (CAP-1).

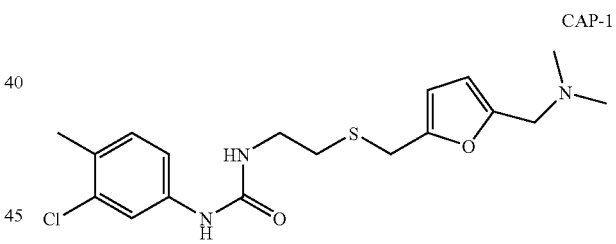

CAP-1

Thus conservatively assuming that cytosolic drug concentrations in the budding virus and cells are equal (100 μM), the percentage of viral CAP-1 molecules bound to CA can be estimated by standard mass action calculations which affords a value for the concentration of bound CAP-1 ([CA:CAP-1]) of 94 μM. This indicates that 94% of the CAP-1 molecules in immature virions (100 μM dose) should be bound to Gag, and that binding to as few as approximately 25 molecules of Gag per virion is sufficient to inhibit core assembly during viral maturation.

Notable interactions between CA and the inhibitor CAP-1 include the interaction of the aromatic ring of Tyr 145 and the furan of CAP-1; the chlorine of the aromatic ring in CAP-1 and the hydrophobic sidechain of Ile 37; the interaction of the sulfur and the hydroxyl group of Ser 146; and the hydroxyl sidechain of Ser 33 and the nitrogen of the dimethylaminomethyl substituent on the 5-position of the furan of CAP 1. Other ureas including those described in the present application may possess functionally very similar interactions with the capsid protein.

Data from examination of the multidimensional NMR spectra of the capsid protein in the presence of the ligands CAP-1 and its structural homologues demonstrate the existence of a potentially high affinity binding site for ligands. A multiplicity of specific and selective interactions were unexpectedly found which not only demonstrate the existence of such a site, but help to suggest how very high affinity ligands might be designed for the site.

It has been postulated that several structural features present in the CAP-1 ligand are relevant to ligand binding at the high affinity site. A substituted phenyl or other aryl group on one side of the molecule, which contains a relatively bulky substituent is desirable. In CAP-1, the chlorine atom serves this purpose. However, experimental data combined with model fitting suggest that the use of a Br- or even I-atom might increase the affinity of binding. The relative position of the sulfur atom in CAP-1 is also significant. It is probable that using a different oxidation state of the sulfur would not lend itself to activity in the present system. This is true for a sulfone or sulfonamide.

In addition to compounds and pharmaceutically acceptable salts of Formula I, described above, compounds and salts having the same general formula, which is reiterated below, and compounds and salts of Formula I-A and Formula I-B, in which one or more of the following conditions are met are also provided herein:

Formula I-A

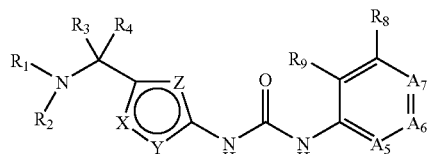

Formula I-B

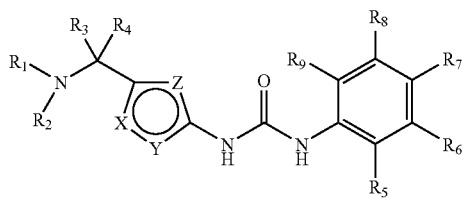

i. Z is S, e.g. the invention provides compounds and salts of Formula II

Formula II

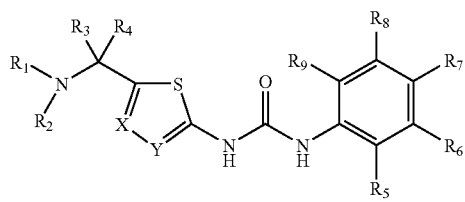

ii. Z is O, e.g. the invention provides compounds and salts of Formula III

Formula III

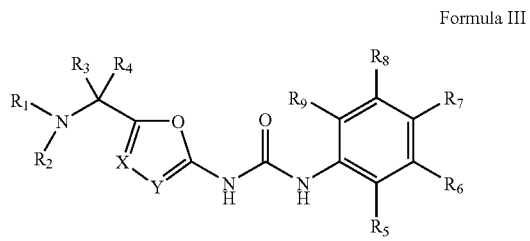

iii. Y is N, e.g. the invention provides compounds and salts of Formula IV and V.

Formula IV

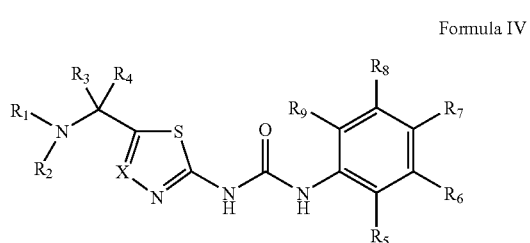

Formula V

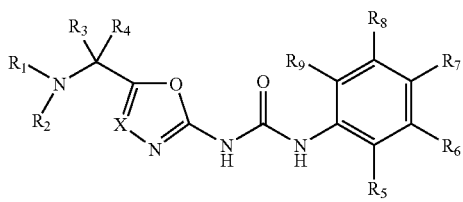

iv. X is CR', e.g. the invention provides compounds and salts of Formula VI–IX.

Formula VI

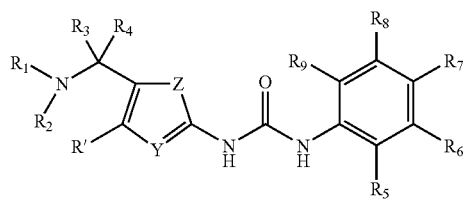

Formula VII

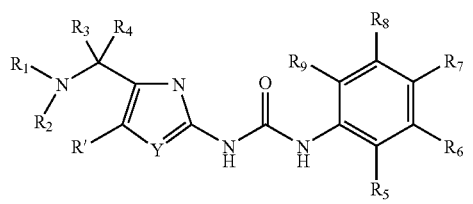

Formula VIII

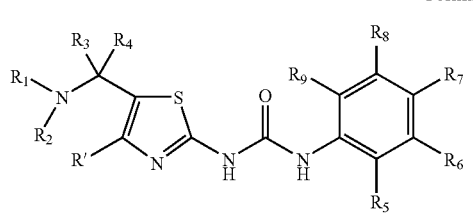

-continued

Formula IX

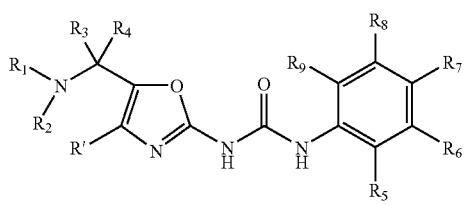

v. Z is N, e.g. the invention provides compounds and salts of Formula X.

Formula X

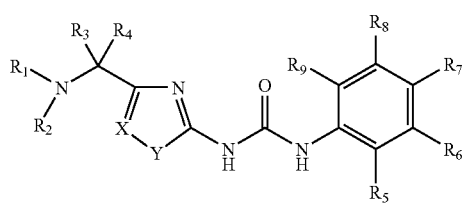

vi. Y is S or O, e.g. the invention provides compounds and salts of Formula XI and XII.

Formula XI

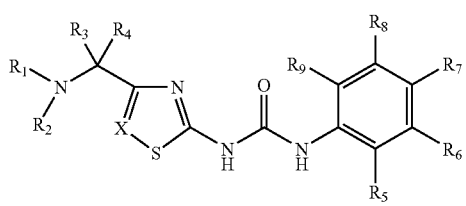

Formula XII

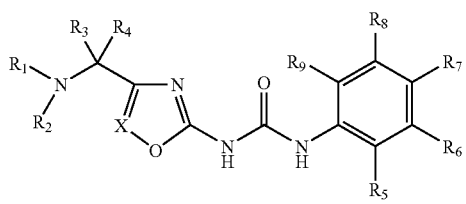

vii. Z is N, Y is optionally S or O, and X is CR', e.g. the invention provides compounds and salts of Formula XIII and XIV.

Formula XIII

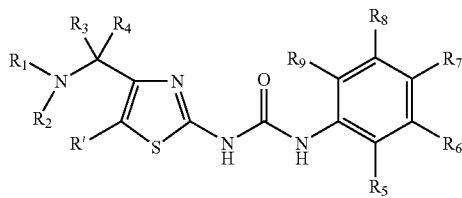

Formula XIV

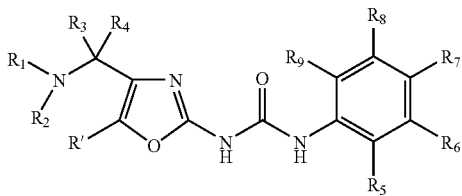

viii. R is hydrogen, $C_1$–$C_4$alkyl, or $C_2$–$C_4$alkenyl; and Each R' is independently hydrogen, halogen, hydroxy, $C_1$–$C_4$alkyl, $C_2$–$C_4$alkenyl, $C_2$–$C_4$alkynyl, $C_1$–$C_4$alkoxy, mono- or di- ($C_1$–$C_4$alkyl)amino, $C_2$–$C_4$alkanoyl, $C_2$–$C_4$alkoxycarbonyl, $C_1$–$C_2$haloalkyl, or $C_1$–$C_2$haloalkoxy.

ix. R is hydrogen or methyl; and each R' is independently hydrogen, halogen, methoxy, or methoxy.

x. R and R' are both hydrogen.

xi. $R_1$ and $R_2$ are independently hydrogen, or $C_1$–$C_6$alkyl, $C_2$–$C_6$alkenyl, $C_2$–$C_6$alkynyl, ($C_3$–$C_7$cycloalkyl)$C_0$–$C_2$alkyl, (heterocycloalkyl)$C_0$–$C_2$alkyl, or (phenyl)$C_0$–$C_2$alkyl, each of which is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

xii. $R_1$ and $R_2$ are independently hydrogen, or $C_1$–$C_6$alkyl, $C_2$–$C_4$alkenyl, $C_2$–$C_6$alkynyl, ($C_3$–$C_7$cycloalkyl)$C_0$–$C_2$alkyl, (heterocycloalkyl)$C_0$–$C_2$alkyl, or (phenyl)$C_0$–$C_2$alkyl, each of which is substituted with 0 to 3 substituents independently chosen from halogen, hydroxy, amino, oxo, —(C=O)NH$_2$, $C_1$–$C_2$alkyl, $C_1$–$C_2$alkoxy, mono- and di-($C_1$–$C_2$alkyl)amino, $C_1$–$C_2$haloalkyl, and $C_1$–$C_2$haloalkoxy.

xiii. $R_1$ is methyl; and $R_2$ is $C_2$–$C_6$alkyl or $C_3$–$C_6$cycloalkyl.

xiv. $R_1$ and $R_2$ are taken together to form a monocyclic or bicyclic heterocycle, which heterocycle is saturated, partially unsaturated, or aromatic, and is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

xv. $R_1$ is methyl or ethyl and $R_2$ is methyl, benzyl, or a group of the formula

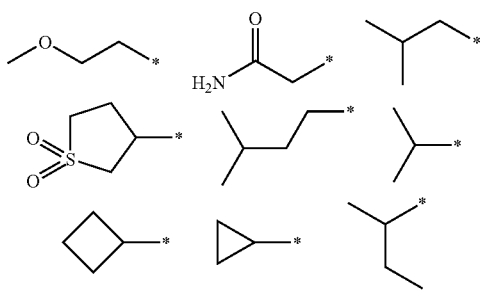

where an asterisk (*) denotes the point of attachment of the $R_2$ group to Nitrogen, or $R_1$ and $R_2$ are joined to form a piperidinyl, pyrrolidinyl, or azetidinyl group.

xvi. Compounds and salts of Formula XV are provided herein

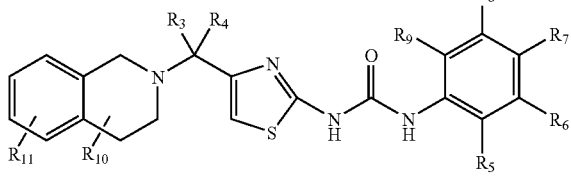

Formula XV within Formula XV, $R_{10}$ and $R_{11}$ together represent 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

xvii. X is NR or CR'; and $R_2$ is taken together with X to form a 5 to 7 membered heterocyclic ring, which is partially unsaturated or aromatic, and is substituted with 0 to 3 substituents independently chosen from halogen, hydroxy, cyano, amino, oxo, $C_1$–$C_4$alkyl, $C_1$–$C_4$alkoxy, mono- and di-($C_1$–$C_4$alkyl)amino, $C_1$–$C_2$haloalkyl, and $C_1$–$C_2$haloalkoxy.

xviii. Compounds and salts of formula XVI are provided herein

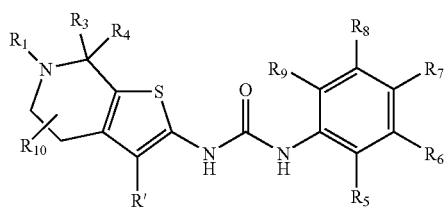

Formula XVI wherein, $R_{10}$ represents 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

xix. $R_3$ and $R_4$ are independently hydrogen, halogen, $C_1$–$C_2$alkyl, or $C_1$–$C_2$alkoxy.

xx. $R_3$ and $R_4$ are independently hydrogen or methyl.

xxi. $A_5$ is N, $A_6$ is $CR_6$, and $A_7$ is $CR_7$, e.g. Compounds and salts of Formula XVII are provided herein:

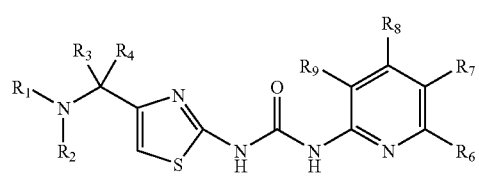

Formula XVII xxii. $A_5$ is $CR_5$, $A_6$ is N, and $A_7$ is $CR_7$, e.g. Compounds and salts of Formula XVIII are provided herein:

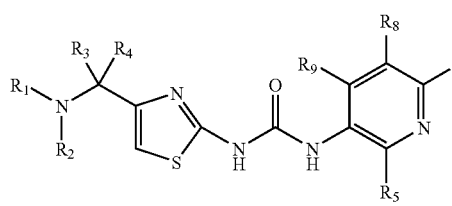

Formula XVIII xxiii. $A_5$ is $CR_5$, $A_6$ is $CR_6$, and $A_7$ is N, e.g. Compounds and salts of Formula XIX are provided herein:

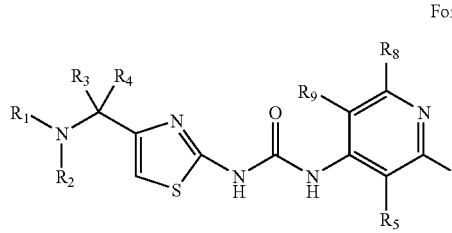

Formula XIX xiv. Compounds and salts of Formula I in which $A_5$ is $CR_5$, $A_6$ is $CR_6$, and $A_7$ is $CR_7$ are provided herein.

xxv. $A_5$–$A_7$ are not N; and $R_5$, $R_8$, and $R_9$ are independently hydrogen, halogen, methyl, ethyl, methoxy, ethoxy, trifluoromethyl, or trifluoromethoxy.

xxvi. $A_5$–$A_7$ are not N; and $R_5$, $R_8$, and $R_9$ are all hydrogen.

xxvii. $A_5$–$A_7$ are not N; and $R_6$ and $R_7$ are independently (i) hydrogen, halogen, hydroxy, cyano, amino, or nitro; or (ii) $C_1$–$C_6$alkyl, $C_2$–$C_6$alkenyl, $C_2$–$C_6$alkynyl, $C_1$–$C_6$alkoxy, $C_2$–$C_6$alkanoyl, ($C_3$–$C_7$cycloalkyl)$C_0$–$C_2$alkyl, (heterocycloalkyl)$C_0$–$C_2$alkyl, (phenyl)$C_0$–$C_2$alkyl, mono- or di-($C_1$–$C_6$alkyl)amino, $C_1$–$C_2$haloalkyl, or $C_1$–$C_2$haloalkoxy; each of which is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

xxviii. $A_5$–$A_7$ are not N; and $R_6$ and $R_7$ are independently hydrogen, halogen, hydroxy, cyano, amino, nitro, $C_1$–$C_6$alkyl, $C_2$–$C_6$alkenyl, $C_2$–$C_6$alkynyl, $C_1$–$C_6$alkoxy, $C_2$–$C_6$alkanoyl, ($C_3$–$C_7$cycloalkyl)$C_0$–$C_2$alkyl, (heterocycloalkyl)$C_0$–$C_2$alkyl, (phenyl)$C_0$–$C_2$alkyl, mono- or di-($C_1$–$C_6$alkyl)amino, $C_1$–$C_2$haloalkyl, or $C_1$–$C_2$haloalkoxy.

A5–$A_7$ are not N; and $R_6$ and $R_7$ are independently hydrogen, halogen, hydroxy, amino, cyano, $C_1$–$C_4$alkyl, $C_2$–$C_4$alkenyl, $C_2$–$C_4$alkynyl, $C_1$–$C_4$alkoxy, mono- or di-($C_1$–$C_2$alkyl)amino, ($C_1$–$C_2$alkyl)amino, $C_1$–$C2$haloalkyl, or $C_1$–$C_2$haloalkoxy.

xxx. $A_5$–$A_7$ are not N; and $R_6$ and $R_7$ are independently hydrogen, halogen, cyano, methyl, methoxy, propynyl, or trifluoromethyl.

xxxi. $A_5$–$A_7$ are not N; and $R_6$ is halogen and $R_7$ is methyl.

xxxii. $A_5$–$A_7$ are not N; and $R_5$ is joined with $R_6$ to form a phenyl ring or a 5- or 6-membered heteroaryl ring having from 1 to 3 heteroatoms independently chosen from N, O, and S, each of which is substituted with 0 to 2 substituents independently chosen from halogen, cyano, $C_1$–$C_2$alkyl, $C_1$–$C_2$alkoxy, trifluoromethyl, and trifluoromethoxy.

xxxiii. $A_5–A_7$ are not N; and $R_5$ is joined with $R_6$ to form an unsubstituted 5-membered heteroaryl ring having 2 or 3 heteroatoms independently chosen from N, O, and S.

xxxiv. $A_5–A_7$ are not N; and $R_5$ is joined with $R_6$ to form an unsubstituted 1,2,5-thiazolyl, 1,2,5-oxadiazolyl, or imidazolyl ring.

xxxv. $A_5–A_7$ are not N; and $R_5$ is joined with $R_6$ as in condition xxxii, xxxiii, or xxxiv and $R_7$, $R_8$, and $R_9$ are independently hydrogen, halogen, methyl, ethyl, methoxy, ethoxy, trifluoromethyl, or trifluoromethoxy.

xxxvi. $A_5–A_7$ are not N; and $R_5$ is joined with $R_6$ as in condition xxxii, xxxiii, or xxxiv and $R_7$, $R_8$, and $R_9$ are all hydrogen.

xxxvii. $A_5–A_7$ are not N; and $R_6$ and $R_7$ are joined to form a phenyl ring or a 5-or 6-membered heteroaryl ring having 1 or 2 heteroatoms independently chosen from N, O, and S, each of which is substituted with 0 to 3 substituents independently chosen from halogen, hydroxy, cyano, amino, nitro, —(C=O)$NH_2$, $C_1–C_4$alkyl, $C_1–C_4$alkoxy, $C_2–C_4$alkanoyl, mono- and di-($C_1–C_4$alkyl)amino, $C_1–C_2$haloalkyl, and $C_1–C_2$haloalkoxy.

xxxviii. $A_5–A_7$ are not N; and $R_6$ and $R_7$ are joined to form a phenyl ring or a 5- or 6-membered heteroaryl ring having 1 or 2 heteroatoms independently chosen from N, O, and S, each of which is substituted with 0 to 3 substituents independently chosen from halogen, cyano, $C_1–C_2$alkyl, $C_1–C_2$alkoxy, trifluoromethyl, and trifluoromethoxy.

xxxix. $A_5–A_7$ are not N; and $R_6$ and $R_7$ are joined to form a phenyl, pyridyl, thienyl, pyrrolyl, imidazolyl, or thiazolyl ring, each of which is substituted with 0 to 3 substituents independently chosen from halogen, cyano, $C_1–C_2$alkyl, $C_1–C_2$alkoxy, trifluoromethyl, and trifluoromethoxy.

xl. $A_5–A_7$ are not N; and $R_5$, $R_8$, and $R_9$ are all hydrogen; $R_6$ is hydrogen, methyl, methoxy, chloro, bromo, fluoro, iodo, trifluoromethyl, cyano, acetyl, 3-hydroxyprop-1-ynyl, prop-1-ynyl, or furanyl; and $R_7$ is hydrogen, hydroxy, hydroxymethyl, methyl, methoxy, cyano, chloro, or fluoro.

Any of the above conditions may be combined, so long as a stable compounds of Formula I results. For example the invention includes compounds of Formula I in which condition xix. ($R_3$ and $R_4$ are independently hydrogen, halogen, $C_1–C_2$alkyl, or $C_1–C_2$alkoxy) and condition xxx. ($R_6$ and $R_7$ are independently hydrogen, halogen, cyano, methyl, methoxy, propynyl, or trifluoromethyl) are both met.

PHARMACEUTICAL COMPOSITIONS

Compounds and salts of Formula I can be administered as the neat chemical, but are preferably administered as a pharmaceutical composition or formulation. Accordingly, the invention provides pharmaceutical formulations comprising a compound or pharmaceutically acceptable salt of Formula I, together with one or more pharmaceutically acceptable carrier, excipients, adjuvant, diluent, excipient, or other ingredient.

Compounds of general Formula I may be administered orally, topically, parenterally, by inhalation or spray, sublingually, transdermally, via buccal administration, rectally, as an ophthalmic solution, or by other means, in dosage unit formulations containing conventional non-toxic pharmaceutically acceptable carriers, excipients, adjuvants, and vehicles.

A pharmaceutical composition comprising a compound or salt of Formula I wherein the composition is formulated as an injectable fluid, an aerosol, a cream, a gel, a pill, a capsule, a tablet, a syrup, a transdermal patch, or an ophthalmic solution is provided herein.

In addition to the subject compound, the compositions of the invention may contain a pharmaceutically acceptable carrier, one or more compatible solid or liquid filler diluents or encapsulating substances, which are suitable for administration to an animal. Carriers must be of sufficiently high purity and sufficiently low toxicity to render them suitable for administration to the animal being treated. The carrier can be inert or it can possess pharmaceutical benefits of its own. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

In particular, pharmaceutically acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil.

Optional active agents may be included in a pharmaceutical composition, which do not substantially interfere with the activity of the compound of the present invention.

Effective concentrations of one or more of the compounds of the invention including pharmaceutically acceptable salts, esters or other derivatives thereof, are mixed with one or more suitable pharmaceutical carrier, excipient, adjuvant, or vehicle. In instances in which the compounds exhibit insufficient solubility, methods for solubilizing compounds may be used. Such methods are known to those of skill in this art, and include, but are not limited to using cosolvents, such as dimethylsulfoxide (DMSO), using surfactants, such as Tween, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of Formula I, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder or condition treated and may be empirically determined.

The pharmaceutical compositions containing compounds of general Formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations.

Oral formulations contain between 0.1 and 99% of a compound of the invention and usually at least about 5% (weight %) of a compound of the present invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Acceptable vehicles and solvents include water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of Formula I may be administered parenterally in a sterile medium. Parenteral administration includes subcutaneous injections, intravenous, intramuscular, intrathecal injection, or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier comprises at least about 90% by weight of the total composition.

Topical Formulations

Compounds of the invention may be formulated for local or topical application, such as for topical application to the skin and mucous membranes, such as in the eye, in the form of gels, creams, and lotions and for application to the eye or for intracisternal or intraspinal application. Topical compositions of the present invention may be in any form including, for example, solutions, creams, ointments, gels, lotions, milks, cleansers, moisturizers, sprays, skin patches, and the like.

Such solutions may be formulated as 0.01% –10% isotonic solutions, pH about 5–7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, iso-propyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fillers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorption enhancers.

Pharmaceutical compositions of the invention may also contain additional active agents chosen from a wide variety of molecules, which can function in different ways to enhance the antimicrobial or therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

In all of the foregoing embodiments the compound of the invention can be administered alone or as mixtures, and the compositions may further include additional drugs or excipients as appropriate for the indication.

Packaged Formulations

The invention includes packaged pharmaceutical formulations. Such packaged formulations include a pharmaceutical composition containing one or more compounds or salts of Formula I in a container and optionally include instructions for using the composition to treat an animal (typically a human patient) suffering from a viral infection, such as an HIV infection, and including an HIV-1 or HIV-2 infection, or to prevent a viral infection in an animal. In certain embodiments the instructions are instructions for using the composition to treat a patient suffering from an HIV-1 infection.

METHODS OF TREATMENT

The invention includes methods of preventing and treating viral infections by administering a therapeutically effective amount of one or more compounds of Formula I to an animal at risk for a viral infection or suffering from a viral infection. Methods disclosed herein fro treating viral infections include methods of treating retroviral infections including lentivirus infections such as HIV infections, including HIV-1 and HIV-2 infections.

Viruses having capsid proteins include:

Arenaviruses

Bunyaviridae, such as bunyaviruses, hanta viruses, nairoviruses, and phlebovirus Coronaviridae, such as coronaviruses, including the SARS virus, and toroviruses Cystoviridae Filoviridae, including the Marburg virus and Ebola viruses Flaviviridae, such as flavivirus, pestiviruses, and Hepatitis C virus. Flaviviruses include tick borne encephalitis, yellow fever and dengue fever virus.

Hepadnaviridae, such as Hepatitis B viruses

Herpesviridae, such as simpleviruses, varicelloviruses, and cytomegaloviruses

Orthomyxoviridae, such as influenza viruses

Paramyxoviridae, such as paramyxoviruses, morbilliviruses, and pneumonviruses

Picornaviruses, such as enteroviruses, poliovirus, rhinoviruses, hepatitis A virus, encephalomyocarditis virus, and aphthovirus Retrovirus, including lentiviruses, Human spumavirus, and oncoviruses. Lentiviruses include HIV viruses, and Togaviridae, including rubella virus.

Methods of preventing or treating HIV-1 infections and methods of treating AIDS are particularly included herein. The animal may be a fish, amphibian, reptile or bird, but is preferably a mammal. In many embodiments the animal is a human patient. Methods of treating HIV-1 infections in human patients are particularly preferred.

In some circumstances an effective amount of a compound of Formula I may be an amount sufficient to reduce the symptoms of the viral infection. Alternatively an effective amount of a compound of Formula I may be an amount sufficient to significantly reduce the amount of virus particles or antibodies against the virus detectable in a patient's tissues or bodily fluids.

Methods of treatment also include inhibiting viral capsid formation, especially HIV capsid formation, in vivo, in an animal infected with a virus, such as HIV-1 or suffering from AIDS, by administering a sufficient concentration of a compound of Formula I to inhibit viral capsid formation in vitro. Methods of treatment also include reducing mortality of HIV-1 infection and/or AIDS by administering a therapeutically effective amount of a compound of Formula I to a human patient infected with HIV-1 Reduction in mortality may be any accepted means form measuring reduction in mortality or increased survival rates. For example a reduction in mortality may be an larger 2 year or 5 year survival rate in HIV-1 infected patients administered a compound of Formula I compared to HIV-1 infected patients not administered a compound of Formula I and not given any other treatment for HIV-1 infection. By "sufficient concentration" of a compound administered to the animal is meant the concentration of the compound available in the animal's system to prevent or combat the infection. Such a concentration by be ascertained experimentally, for example by assaying blood concentration of the compound, or theoretically, by calculating bioavailability. The amount of a compound sufficient to inhibit bacterial survival in vitro may be determined, for example, with an 2D NMR assay for compound binding to capsid protein such as the assay given in Example 5, or the cytoprotection assay given in Example 6a, both of which follow.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most HIV-1 infections, a dosage regimen of 4 times daily or less is preferred and a dosage regimen of 1 or 2 times daily or less is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

EXAMPLES

Example 1

PREPARATION OF 1-(3-CHLORO-4-METHYLPHENYL)-3-(4-((ISOPROPYL(METHYL)AMINO)METHYL)THIAZOL-2-YL)UREA
(Compound 1)

Step 1. 4-((isopropyl(methyl)amino)methyl)thiazol-2-amine

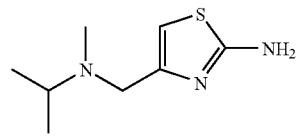

N-methyl-N-isopropylamine (3.02 g, 41 mmol) is added to a suspension of 2-amino-4-chloromethylthiazole hydrochloride (0.185 g, 1.0 mmol) in 15 mL ethanol. The reaction mixture is allowed to stand at room temperature for 4 days. The mixture was poured into aqueous potassium carbonate. The resulting aqueous suspension is extracted with dichloromethane. The organic layer is dried over $MgSO_4$ and condensed to brown oil.

Step 2. 1-(3-chloro-4-methylphenyl)-3-(4-((isopropyl(methyl)amino)methyl)thiazol-2-yl)urea

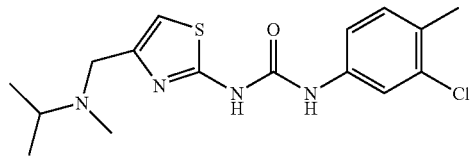

4-((isopropyl(methyl)amino)methyl)thiazol-2-amine (18 mg, 0.1 mmol) in dichloromethane (0.5 mL) is added to 3-chloro-4-methylphenyl isocyanate (16.7 mg, 0.1 mmol) in dichloromethane (0.5 mL). The resulting reaction mixture is shaken at room temperature for 1 hour. The solvent is evaporated under vacuum. The residue is purified by preparative LC to yield a brown glass LCMS, retention time: 1.87 min, M+H$^+$: 353. H$^1$-NMR (DMSO, σ ppm): 10.82 (s, 1H), 9.51–9.41 (s, br, 1H), 9.31 (s, 1H), 7.70 (s, 1H), 7.33 (s, 1H), 7.18–7.30 (m, 2H), 4.11–4.39 (m, 2H), 2.69 (d, 3H), 2.28 (s, 3H), 1.29 (t, 6H)).

Example 2

PREPARATION OF 1-(4-((ISOPROPYL(METHYL)AMINO)METHYL)THIAZOL-2-YL)-3-P-TOLYLUREA TRIFLUOROACETIC ACID
(Compound 2)

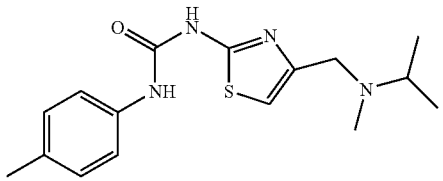

4-Methylaniline (13.3 mg, 0.1 mmol) is first mixed with triethylamine (0.5 mL, 0.5 M in dichloromethane, 0.25 mmol). The above mixture is added slowly with shaking to triphosgene (10 mg, 0.033 mmol) in dichloromethane (0.5 mL) at room temperature. The resulting mixture is shaken at room temperature for 1 hour. Then 4-((isopropyl(methyl)amino)methyl)thiazol-2-amine (18 mg, 0.1 mmol) in dichloromethane (0.5 mL) is added. The resulting mixture is shaken at room temperature for 1 hour. The solvent is evaporated under vacuum. The residue is purified by preparative LC to yield a brown glass. LCMS, retention time: 1.65 min, M+H$^+$: 319.

Example 3

PREPARATION OF 1-(4-((ALLYL(METHYL)AMINO)METHYL)THIAZOL-2-YL)-3-(3-CHLORO-4-METHYLPHENYL)UREA TRIFLUOROACETIC ACID. (Compound 3)

Step 1. 4-((allyl(methyl)amino)methyl)thiazol-2-amine

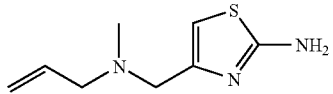

N-allyl-N-methylamine (7.0 mg, 0.1 mmol), 2-amino-4-chloromethylthiazole hydrochloride (18.5 mg, 0.1 mmol), and potassium carbonate (30 mg, 0.21 mmol) are shaken in ethanol (1 mL) at room temperature for 18 hours. The mixture is filtered and the filtrate was condensed under vacuum.

Step 2. 1-(4-((allyl(methyl)amino)methyl)thiazol-2-yl)-3-(3-chloro-4-methylphenyl)urea trifluoroacetic acid

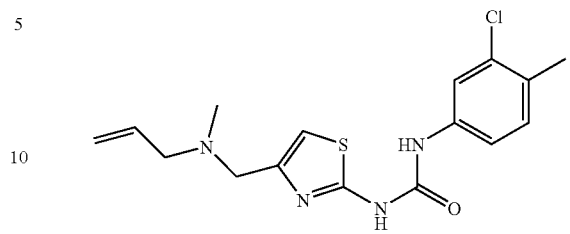

3-Chloro-4-methylphenyl isocyanate (16.7 mg, 0.1 mmol) in dichloromethane (1.0 mL) is added to the above residue of 4-((allyl(methyl)amino)methyl)thiazol-2-amine and the resulting mixture is shaken at room temperature for 30 minutes. The solvent is evaporated under vacuum. The residue is purified by preparative LC to yield a white fluff. LCMS, retention time: 1.00 min, M+H$^+$: 368.

Example 4

PREPARATION OF ADDITIONAL SUBSTITUTED ARYL AMINOMETHYL THIAZOLE UREAS

Additional compounds of Formula I are provided in the tables below.

LC-RT values reported in Table I, Example 4 are HPLC column retention times. A gradient of 30–100% B in 3.00 min was used. Buffer A was 0.1% trifluoroacetic acid in water and buffer B was 0.1% trifluoroacetic acid in acetonitrile. An analytical YMC Pack Pro C18 column was used with a flow rate of 2.5 mL/min. All HPLC/MS analytical runs were run at a wavelength of 220 nm using a Gilson 151 UV/VIS detector followed by a mass spectroscopy with a ThermoFinnigan Surveyor MSQ. This LC-MS method was also used in collecting the LC-MS data reported in Examples 1 to 3.

LC-RT values reported in Table II, Example 4 are HPLC column retention times. An isocratic elution of 0.24 min. at 90:10 A:B followed by a 4 minute linear gradient elution from 90:10 A:B to 10:90 B:A at a flow rate of 2.5 mL/min was used. Buffer A contained 0.1% TFA in H$_2$O, Buffer B contained 0.1% TFA in acetonitrile. HPLC/MS analytical runs were run at a wavelength of 254 nm using a Gilson 151 UV/VIS detector followed by a mass spectroscopy with a ThermoFinnigan Surveyor MSQ (APCI mode).

Biological data: Compounds 4–5, 8–10, 13–15, 17–18, 21–22, 24–27, 29–33, 36–39, and 42–44 were tested in the HSQC assay provided in Example 5 and determined to bind to the HIV-1 capsid protein. Compounds 14, 15, 17, and 38 were tested in the cell viability assay of Example 6 and found to exhibit K$_d$ values of less than 1 mM.

TABLE I

| Cmp. # | STRUCTURE | NAME | LC-RT | MS |
|---|---|---|---|---|
| 4 | 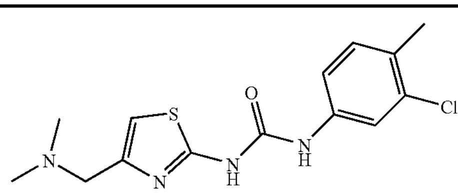 | 1-(3-chloro-4-methylphenyl)-3-(4-((dimethylamino)methyl)thiazol-2-yl)urea | 1.08 | 325 |

TABLE I-continued

| Cmp. # | STRUCTURE | NAME | LC-RT | MS |
|---|---|---|---|---|
| 5 | 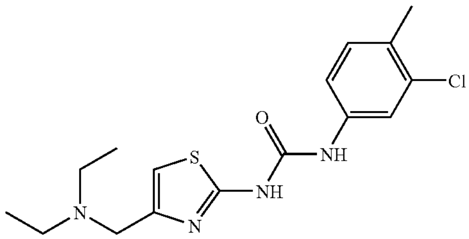 | 1-(3-chloro-4-methylphenyl)-3-(4-((diethylamino)methyl)thiazol-2-yl)urea | 1.19 | 353 |
| 6 | 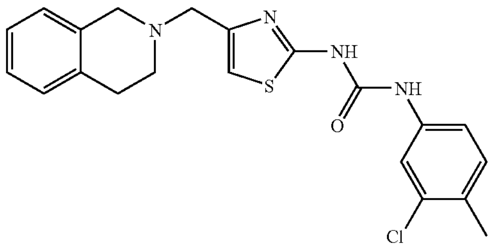 | 1-(3-chloro-4-methylphenyl)-3-(4-((3,4-dihydroisoquinolin-2(1H)-yl)methyl)thiazol-2-yl)urea | 1.28 | 413 |
| 7 | 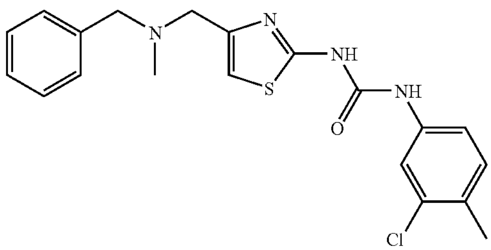 | 1-(4-((benzyl(methyl)amino)methyl)thiazol-2-yl)-3-(3-chloro-4-methylphenyl)urea | 1.40 | 401 |
| 8 | 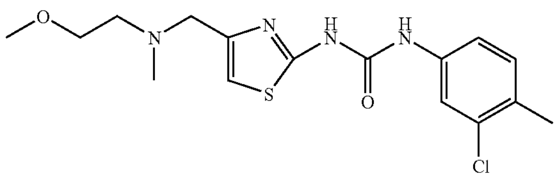 | 1-(3-chloro-4-methylphenyl)-3-(4-(((2-methoxyethyl)(methyl)amino)methyl)thiazol-2-yl)urea | 1.18 | 369 |
| 9 | 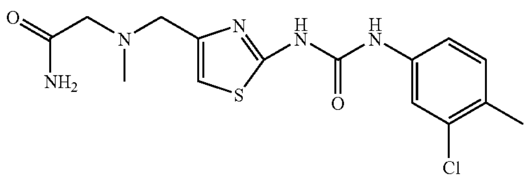 | 1-(4-(((2-amino-2-oxoethyl)(methyl)amino)methyl)thiazol-2-yl)-3-(3-chloro-4-methylphenyl)urea | 1.00 | 368 |
| 10 | 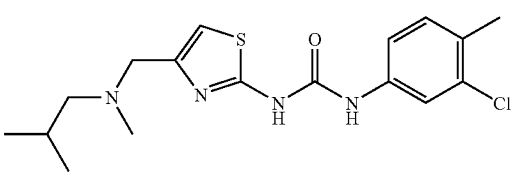 | 1-(3-chloro-4-methylphenyl)-3-(4-((isobutyl(methyl)amino)methyl)thiazol-2-yl)urea | 1.28 | 367 |
| 11 | 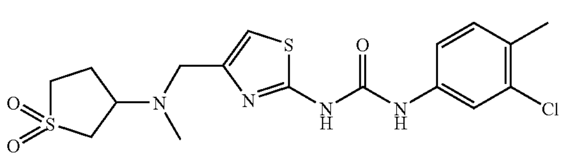 | 1-(3-chloro-4-methyl-phenyl)-3-(4-{[(1,1-dioxo-tetrahydrothiophen-3-yl)methyl-amino]-methyl}-thiazol-2-yl)-urea | 1.16 | 429 |

TABLE I-continued

| Cmp. # | STRUCTURE | NAME | LC-RT | MS |
|---|---|---|---|---|
| 12 | 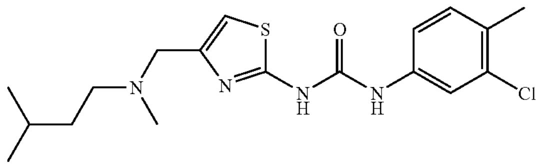 | 1-(3-chloro-4-methylphenyl)-3-(4-((isopentyl(methyl)amino)methyl)thiazol-2-yl)urea | 1.46 | 381 |
| 13 | 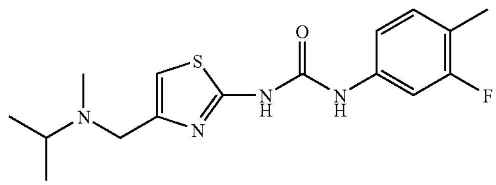 | 1-(3-fluoro-4-methylphenyl)-3-(4-((isopropyl(methyl)amino)methyl)thiazol-2-yl)urea | 1.75 | 337 |
| 14 | 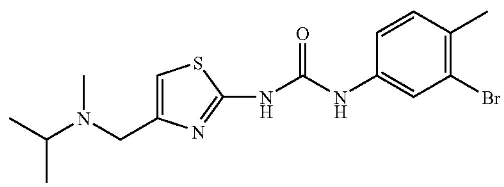 | 1-(3-bromo-4-methylphenyl)-3-(4-((isopropyl(methyl)amino)methyl)thiazol-2-yl)urea | 1.92 | 397 |
| 15 | 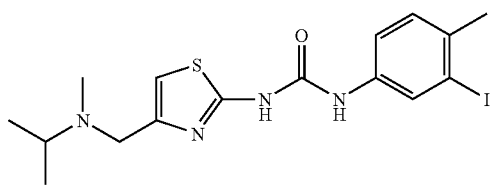 | 1-(3-iodo-4-methylphenyl)-3-(4-((isopropyl(methyl)amino)methyl)thiazol-2-yl)urea | 1.97 | 445 |
| 16 | 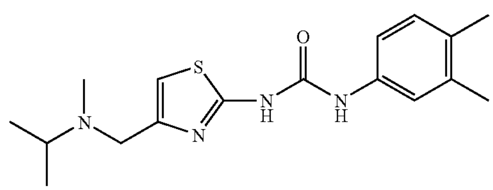 | 1-(3,4-dimethylphenyl)-3-(4-((isopropyl(methyl)amino)methyl)thiazol-2-yl)urea | 1.72 | 333 |
| 17 | 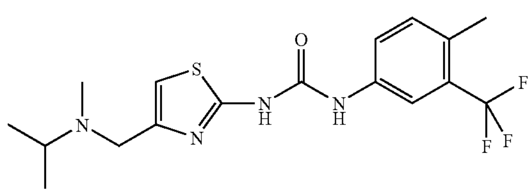 | 1-(4-((isopropyl(methyl)amino)methyl)thiazol-2-yl)-3-(4-methyl-3-(trifluoromethyl)phenyl)urea | 1.96 | 387 |
| 18 | 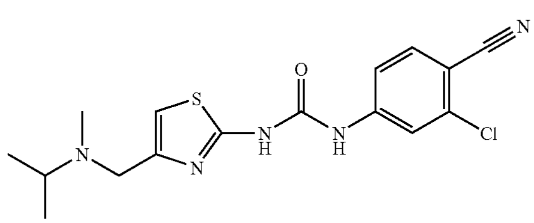 | 1-(3-chloro-4-cyanophenyl)-3-(4-((isopropyl(methyl)amino)methyl)thiazol-2-yl)urea | 1.80 | 364 |
| 19 | 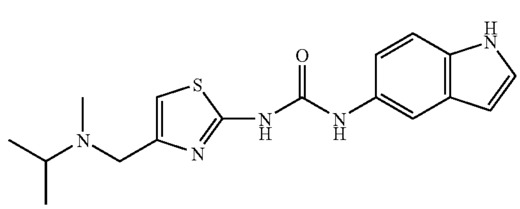 | 1-(1H-indol-5-yl)-3-(4-((isopropyl(methyl)amino)methyl)thiazol-2-yl)urea | 1.41 | 344 |

TABLE I-continued

| Cmp. # | STRUCTURE | NAME | LC-RT | MS |
| --- | --- | --- | --- | --- |
| 20 | 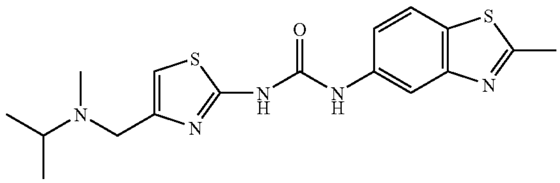 | 1-(4-((isopropyl(methyl)amino)methyl)thiazol-2-yl)-3-(2-methylbenzo[d]thiazol-5-yl)urea | 1.54 | 376 |
| 21 | 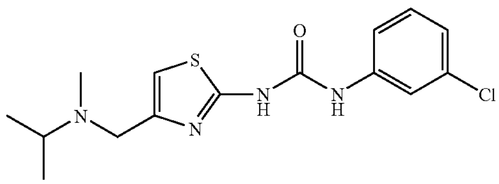 | 1-(3-chlorophenyl)-3-(4-((isopropyl(methyl)amino)methyl)thiazol-2-yl)urea | 1.80 | 339 |
| 22 | 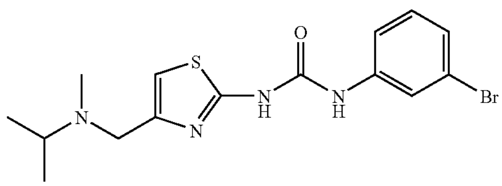 | 1-(3-bromophenyl)-3-(4-((isopropyl(methyl)amino)methyl)thiazol-2-yl)urea | 1.80 | 383 |
| 23 | 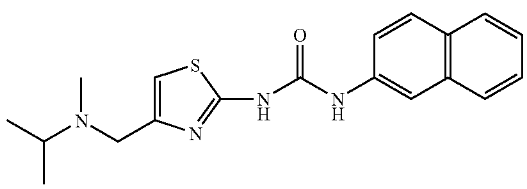 | 1-(4-((isopropyl(methyl)amino)methyl)thiazol-2-yl)-3-(naphthalen-2-yl)urea | 1.85 | 355 |
| 24 | 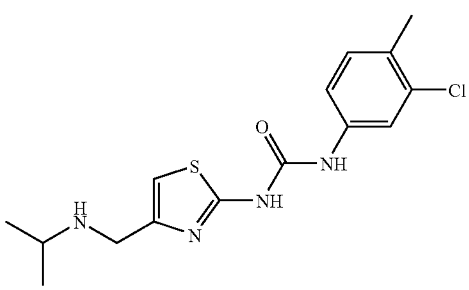 | 1-(3-chloro-4-methylphenyl)-3-(4-((isopropylamino)methyl)thiazol-2-yl)urea | 1.86 | 339 |
| 25 | 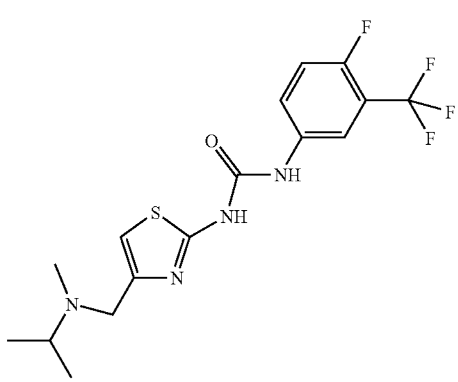 | 1-(4-fluoro-3-(trifluoromethyl)phenyl)-3-(4-((isopropyl(methyl)amino)methyl)thiazol-2-yl)urea | 1.92 | 391 |

TABLE I-continued

| Cmp. # | STRUCTURE | NAME | LC-RT | MS |
|---|---|---|---|---|
| 26 | 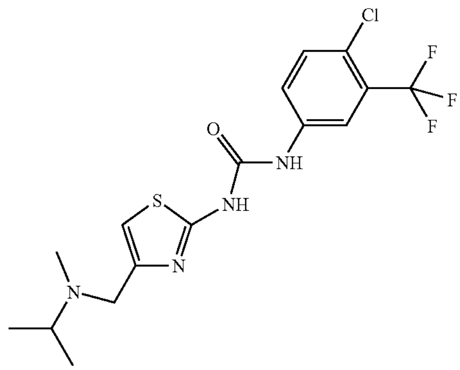 | 1-(4-chloro-3-(trifluoromethyl)phenyl)-3-(4-((isopropyl(methyl)amino)methyl)thiazol-2-yl)urea | 2.06 | 407 |
| 27 | 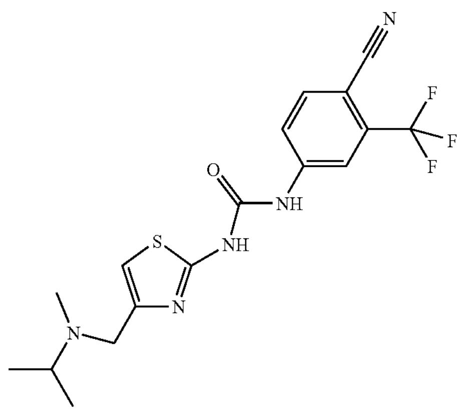 | 1-(4-cyano-3-(trifluoromethyl)phenyl)-3-(4-((isopropyl(methyl)amino)methyl)thiazol-2-yl)urea | 1.95 | 398 |
| 28 | 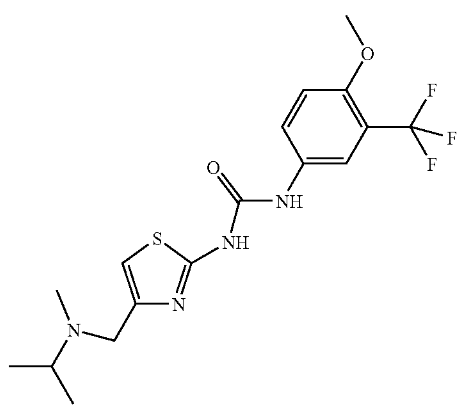 | 1-(4-methoxy-3-(trifluoromethyl)phenyl)-3-(4-((isopropyl(methyl)amino)methyl)thiazol-2-yl)urea | 1.80 | 403 |
| 29 | 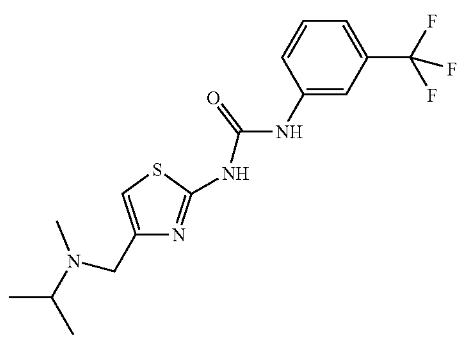 | 1-(3-(trifluoromethyl)phenyl)-3-(4-((isopropyl(methyl)amino)methyl)thiazol-2-yl)urea | 1.86 | 373 |

TABLE I-continued

| Cmp. # | STRUCTURE | NAME | LC-RT | MS |
|---|---|---|---|---|
| 30 | 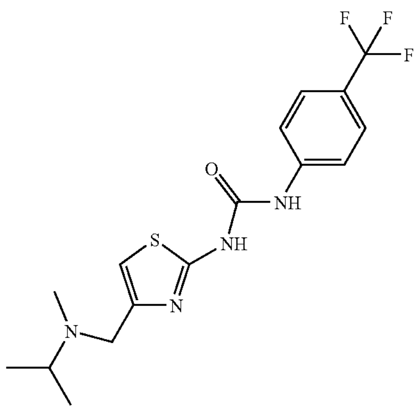 | 1-(4-(trifluoromethyl)phenyl)-3-(4-((isopropyl(methyl)amino)methyl)thiazol-2-yl)urea | 1.89 | 373 |
| 31 | 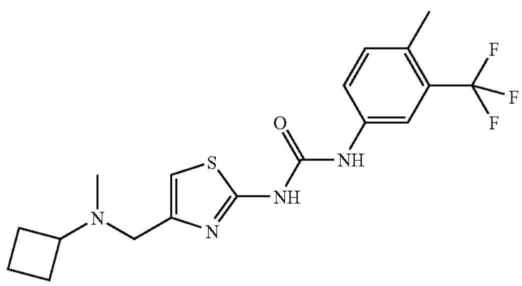 | 1-(4-((cyclobutyl(methyl)amino)methyl)thiazol-2-yl)-3-(4-methyl-3-(trifluoromethyl)phenyl)urea | 2.52 | 399 |
| 32 | 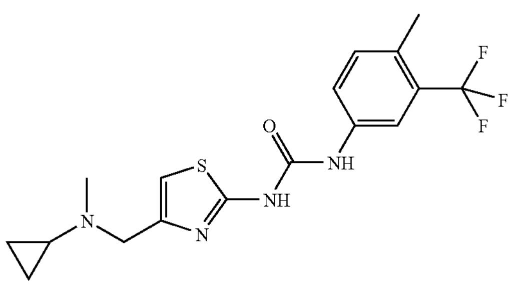 | 1-(4-((cyclopropyl(methyl)amino)methyl)thiazol-2-yl)-3-(4-methyl-3-(trifluoromethyl)phenyl)urea | 2.44 | 385 |
| 33 | 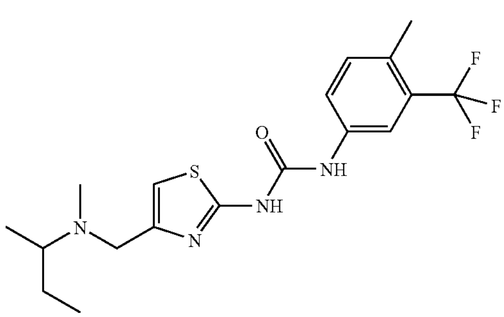 | 1-(4-((sec-butyl(methyl)amino)methyl)thiazol-2-yl)-3-(4-methyl-3-(trifluoromethyl)phenyl)urea | 2.58 | 401 |

TABLE I-continued

| Cmp. # | STRUCTURE | NAME | LC-RT | MS |
| --- | --- | --- | --- | --- |
| 34 | 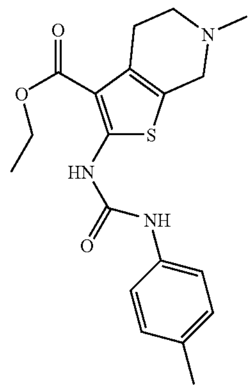 | ethyl 6-methyl-2-(3-p-tolylureido)-4,5,6,7-tetrahydrothieno[2,3-c]pyridine-3-carboxylate | | |
| 35 | 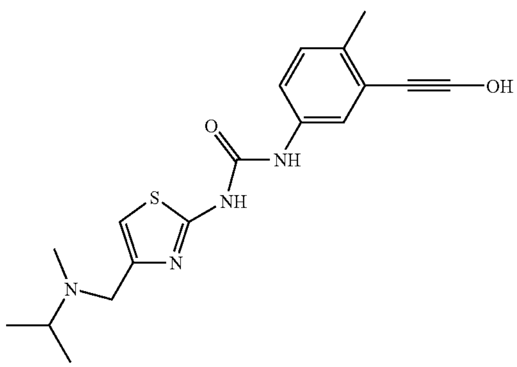 | 1-(3-(3-hydroxyprop-1-ynyl)-4-methylphenyl)-3-(4-((isopropyl(methyl)amino)methyl)thiazol-2-yl)urea | 1.84 | 373 |
| 36 | 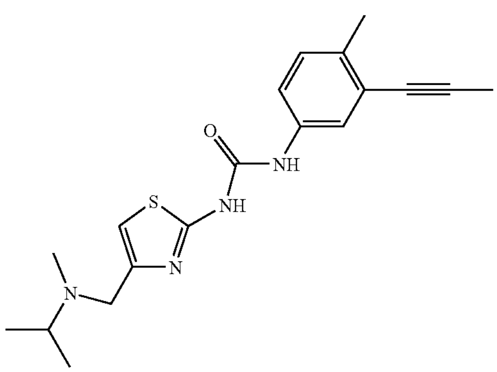 | 1-(4-((isopropyl(methyl)amino)methyl)thiazol-2-yl)-3-(4-methyl-3-(prop-1-ynyl)phenyl)urea | 1.84 | 357 |
| 37 | 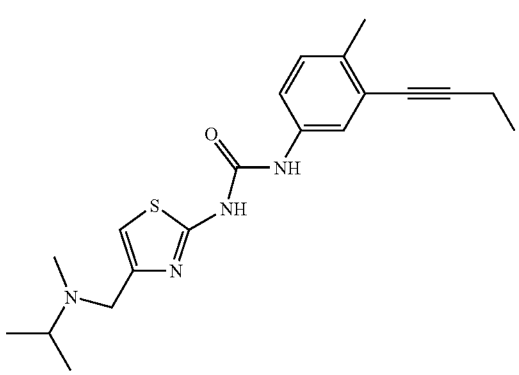 | 1-(3-(but-1-ynyl)-4-methylphenyl)-3-(4-((isopropyl(methyl)amino)methyl)thiazol-2-yl)urea | 2.60 | 371 |

TABLE I-continued

| Cmp. # | STRUCTURE | NAME | LC-RT | MS |
|---|---|---|---|---|
| 38 | 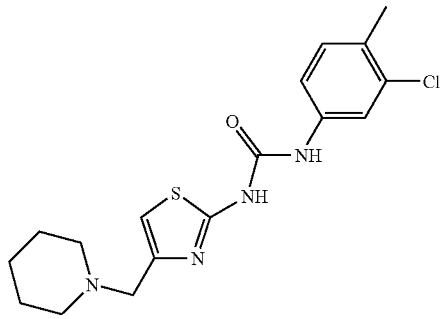 | 1-(3-chloro-4-methylphenyl)-3-(4-(piperidin-1-ylmethyl)thiazol-2-yl)urea | 2.37 | 365 |
| 39 | 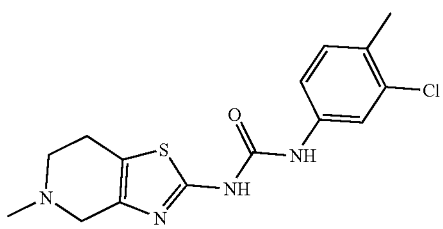 | 1-(3-chloro-4-methylphenyl)-3-(5-methyl-4,5,6,7-tetrahydrothiazolo[4,5-c]pyridin-2-yl)urea | 2.28 | 337 |
| 40 | 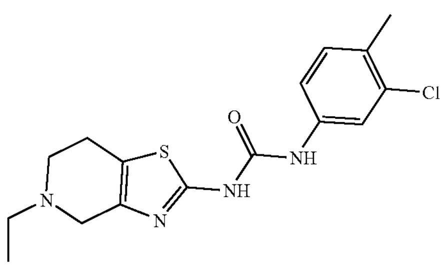 | 1-(3-chloro-4-methylphenyl)-3-(5-ethyl-4,5,6,7-tetrahydrothiazolo[4,5-c]pyridin-2-yl)urea | 2.25 | 351 |
| 41 | 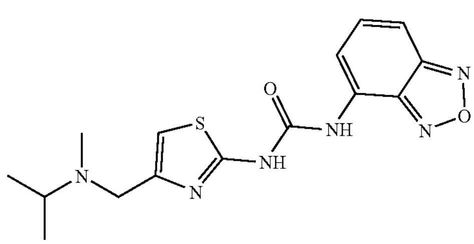 | 1-(benzo[c][1,2,5]oxadiazol-4-yl)-3-(4-((isopropyl(methyl)amino)methyl)thiazol-2-yl)urea | 2.08 | 347 |

TABLE I-continued

| Cmp. # | STRUCTURE | NAME | LC-RT | MS |
|---|---|---|---|---|
| 42 | 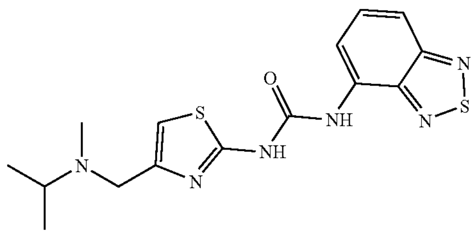 | 1-(benzo[c][1,2,5]thiadiazol-4-yl)-3-(4-((isopropyl(methyl)amino)methyl)thiazol-2-yl)urea | 1.93 | 363 |
| 43 | 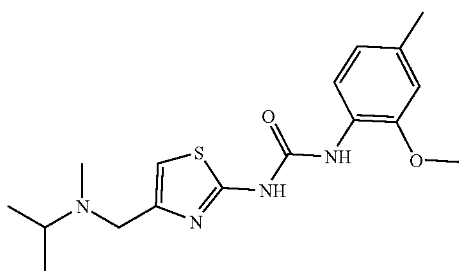 | 1-(4-((isopropyl(methyl)amino)methyl)thiazol-2-yl)-3-(2-methoxy-4-methylphenyl)urea | 2.02 | 349 |
| 44 | 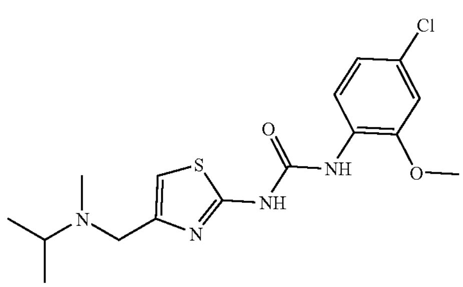 | 1-(4-chloro-2-methoxyphenyl)-3-(4-((isopropyl(methyl)amino)methyl)thiazol-2-yl)urea | 2.37 | 369 |

TABLE II

| Cmp. # | STRUCTURE | NAME | LC-RT | MS | ¹H NMR |
|---|---|---|---|---|---|
| 45 | 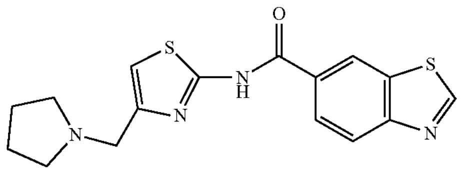 | N-(4-(pyrrolidin-1-ylmethyl)thiazol-2-yl)benzo[d]thiazole-6-carboxamide | | | |
| 46 | 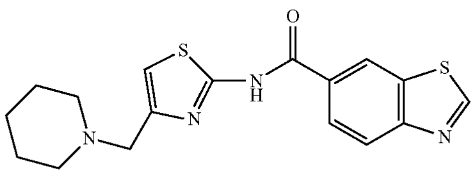 | N-(4-(piperidin-1-ylmethyl)thiazol-2-yl)benzo[d]thiazole-6-carboxamide | | | |
| 47 | 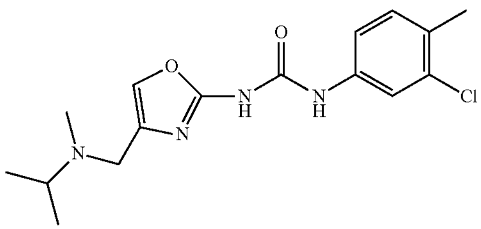 | 1-(3-chloro-4-methylphenyl)-3-(4-((isopropyl(methyl)amino)methyl)oxazol-2-yl)urea | | | |
| 48 | 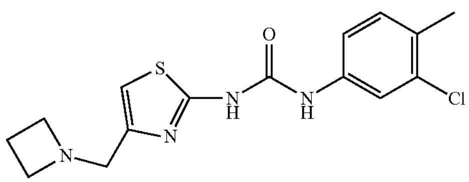 | 1-(4-(azetidin-1-ylmethyl)thiazol-2-yl)-3-(3-chloro-4-methylphenyl)urea | | | |
| 49 | 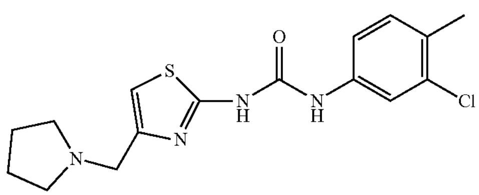 | 1-(3-chloro-4-methylphenyl)-3-(4-(pyrrolidin-1-ylmethyl)thiazol-2-yl)urea | 2.36 | 350.87 | DMSO δ 1.7 (m, 4H, pyrrolidine), 2.3 (s, 3H, CH₃), 2.5 (m, 4H, pyrrolidine), 3.6 (s, 2H, CH₂), 6.8 (s, 1H) thiazole, 7.3 (m, 2H), 7.7 (s, 1H, CH), 9.1 (s, 1H, CH) |

TABLE II-continued

| Cmp. # | STRUCTURE | NAME | LC-RT | MS | ¹H NMR |
|---|---|---|---|---|---|
| 50 | 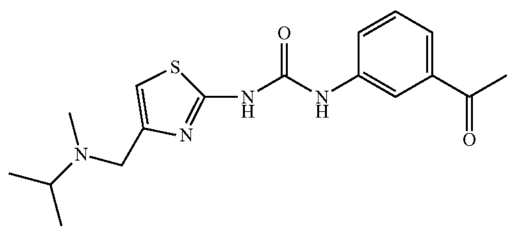 | 1-(3-acetylphenyl)-3-(4-((isopropyl(methyl)amino)methyl)thiazol-2-yl)urea | 1.88 | 346.45 | |
| 51 | 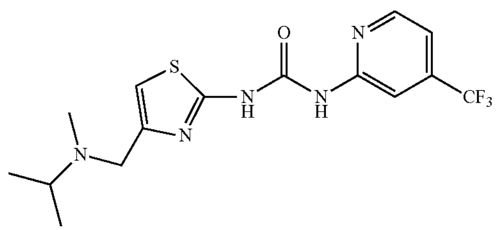 | 1-(4-((isopropyl(methyl)amino)methyl)thiazol-2-yl)-3-(4-(trifluoromethyl)pyridin-2-yl)urea | | | |
| 52 | 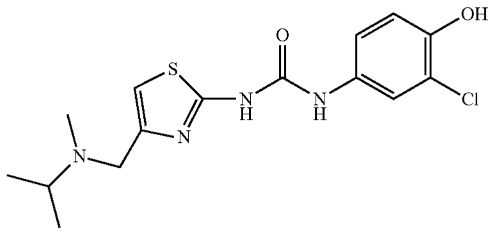 | 1-(3-chloro-4-hydroxyphenyl)-3-(4-((isopropyl(methyl)amino)methyl)thiazol-2-yl)urea | | | |
| 53 | 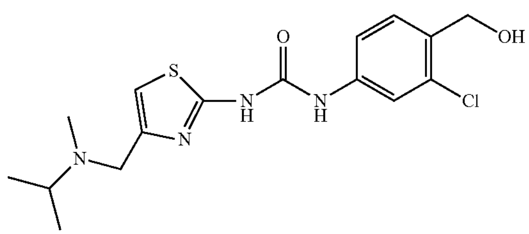 | 1-(3-chloro-4-(hydroxymethyl)phenyl)-3-(4-((isopropyl(methyl)amino)methyl)thiazol-2-yl)urea | 1.77 | 368.88 | DMSO δ 1.0 (m, 6H, CH$_3$), 2.1 (s, 1H), 2.5 (s, 3H, CH$_3$), 2.8 (m, 1H, CH), 4.5 (d, 2H, CH$_2$) 6.8 (s, 1H, thiazolo), 7.4 (m, 1H, CH), 7.7 (m, 1H, CH), 9.1 (m, 1H, CH) |

TABLE II-continued

| Cmp. # | STRUCTURE | NAME | LC-RT | MS | ¹H NMR |
|---|---|---|---|---|---|
| 54 | 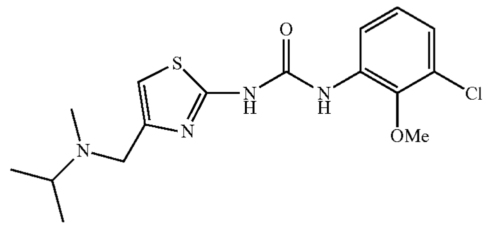 | 1-(3-chloro-2-methoxyphenyl)-3-(4-((isopropyl(methyl)amino)methyl)thiazol-2-yl)urea | 2.26 | 368.88 | DMSO δ 1.3 (m, 6H, CH₃), 2.5 (s, 3H, CH₃), 2.7 (s, 2H, CH₂), 3.8 (s, 3H, CH₃), 4.2 (m, 1H, CH), 7.1 (m, 2H, NH), 7.4 (s, 1H, thiazolo), 8.1 (m, 1H, CH), 9.2 (m, 1H, CH), 11.5 (m, 1H, CH) |
| 55 | 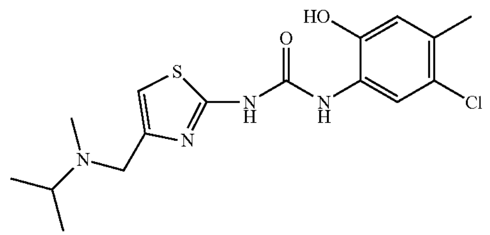 | 1-(5-chloro-2-hydroxy-4-methylphenyl)-3-(4-((isopropyl(methyl)amino)methyl)thiazol-2-yl)urea | | | |
| 56 | 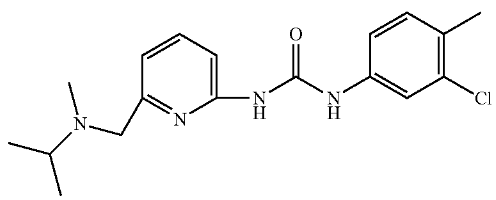 | 1-(3-chloro-4-methylphenyl)-3-(6-((isopropyl(methyl)amino)methyl)pyridin-2-yl)urea | | | |
| 57 | 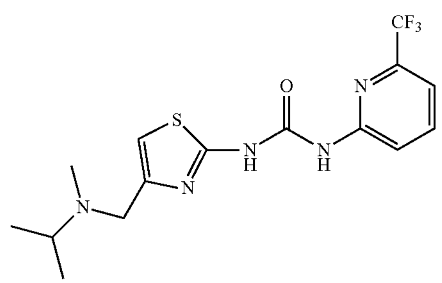 | 1-(4-((isopropyl(methyl)amino)methyl)thiazol-2-yl)-3-(6-(trifluoromethyl)pyridin-2-yl)urea | 2.05 | 373.40 | DMSO δ 1.0 (m, 6H, CH₃), 2.1 (s, 3H, CH₃), 2.5 (s, 2H, CH₂), 2.8 (m, 1H, CH), 6.9 (s, 1H, thiazolo), (m, 1H, CH), 7.5 (m, 1H, CH), 8.1 (m, 1H, CH), 10.1 (m, 1H, CH) |

TABLE II-continued

| Cmp. # | STRUCTURE | NAME | LC-RT | MS | ¹H NMR |
|---|---|---|---|---|---|
| 58 | 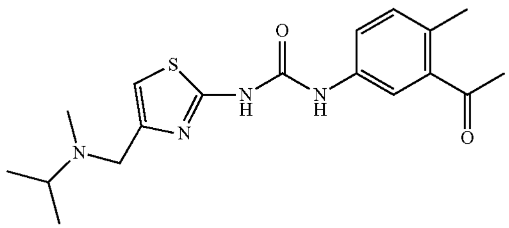 | 1-(3-acetyl-4-methylphenyl)-3-(4-((isopropyl(methyl)amino)methyl)thiazol-2-yl)urea | 2.02 | 360.47 | CDCl$_3$, δ ppm: 1 (m, 6H, CH$_3$); 2.1 (s, 3H, CH$_3$), 2.5 (3H, CH$_3$), 2.6 (3H, (C=O)CH$_3$), 2.8 (m, 1H, CH), 3.5 (s, 2H, CH$_2$), 6.8 (s, 1H, thiazolo), 7.3 (m, 2H, CH), 7.8 (m, 1H, CH) |
| 59 | 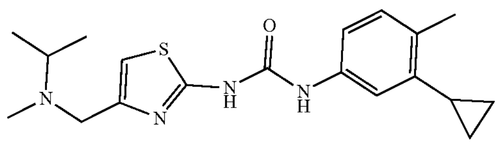 | 1-(3-cyclopropyl-4-methylphenyl)-3-(4-((isopropyl(methyl)amino)methyl)thiazol-2-yl)urea | | | |
| 60 | 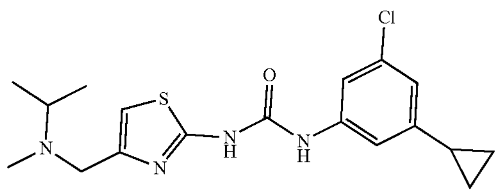 | 1-(3-chloro-5-cyclopropylphenyl)-3-(4-((isopropyl(methyl)amino)methyl)thiazol-2-yl)urea | | | |
| 61 | 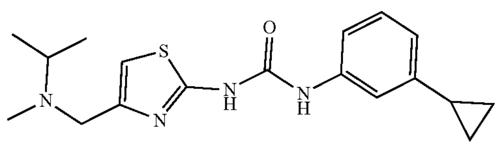 | 1-(3-cycloproylphenyl)-3-(4-((isopropyl(methyl)amino)methyl)thiazol-2-yl)urea | | | |
| 62 | 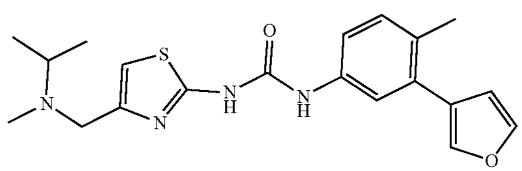 | 1-(3-(furan-3-yl)-4-methylphenyl)-3-(4-(isopropyl(methyl)amino)methyl)thiazol-2-yl)urea | | | 1.0 (m, 6H, CH$_3$), 2.0 (s, 2H, CH$_2$), 2.2 (m, 2H, CH$_3$), 2.5 (s, 3H, CH$_3$), 2.7 (m, 1H, CH$_3$), 3.4 (s, 2H, CH$_2$), 6.6 (s, 1H, thiazolo), 6.8 (m, 1H, CH), 7.1 (m, 1H, CH), 7.3 (m, 1H, CH), 7.4 (s, 1H, CH), 7.6 (s, 1H, CH), 7.8 (s, 1H, CH) |

TABLE II-continued

| Cmp. # | STRUCTURE | NAME | LC-RT | MS | ¹H NMR |
|---|---|---|---|---|---|
| 63 | 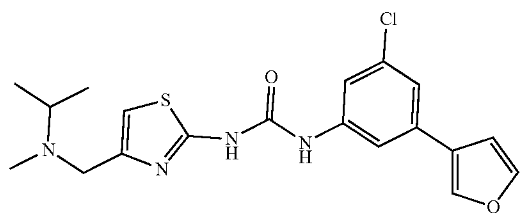 | 1-(3-chloro-5-(furan-3-yl)phenyl)-3-(4-((isopropyl(methyl)amino)methyl)thiazol-2-yl)urea | | | |
| 64 | 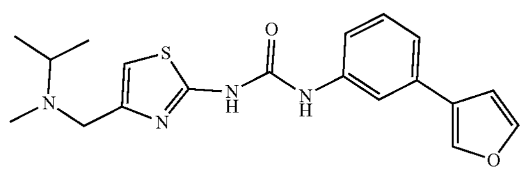 | 1-(3-(furan-3-yl)phenyl)-3-(4-((isopropyl(methyl)amino)methyl)thiazol-2-yl)urea | | | DMSO δ 1 (m, 6H, CH₃), 2.1 (s, 2H), 2.5 (s, 3H, CH₃), 3.5 (s, 1H, CH₂), 6.8 (m, 1H, CH), 7.3 (m, 2H, CH), 7.6 (m, 2H, CH), 7.4 (s, 1H, CH) |
| 65 | 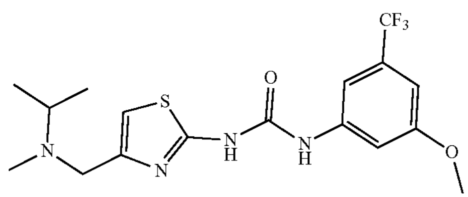 | 1-(4-((isopropyl(methyl)amino)methyl)thiazol-2-yl)-3-(3-methoxy-5-trifluoromethyl)phenyl)urea | 2.53 | 402.43 | DMSO δ 1.1 (m, 6H, CH₃), 2.4 (s, 2H, CH₂), 2.5 (s, 3H, CH₃), 3.1 (m, 1H, CH), 6.8 (s, 1H, thiazolo), 7.0 (s, 1H, CH), 7.2 (s, 1H, CH), 7.4 (s, 1H, CH) |
| 66 | 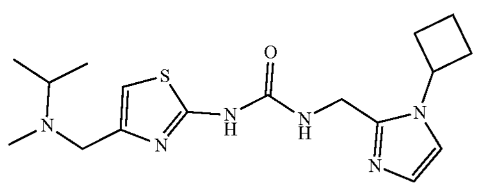 | 1-((1-cyclobutyl-1H-imidazol-2-yl)methyl)-3-(4-((isopropyl(methyl)amino)methyl)thiazol-2-yl)urea | | | |

TABLE II-continued

| Cmp. # | STRUCTURE | NAME | LC-RT | MS | ¹H NMR |
|---|---|---|---|---|---|
| 67 | 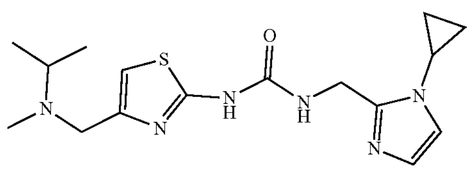 | 1-((1-ethyl-1H-imidazol-2-yl)methyl)-3-(4-((isopropyl(methyl)amino)methyl)thiazol-2-yl)urea | | | |
| 68 | 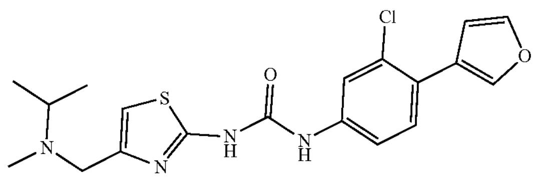 | 1-(3-chloro-4-(furan-3-yl)phenyl)-3-(4-((isopropyl(methyl)amino)methyl)thiazol-2-yl)urea | | | DMSO δ 1.2 (m, 6H, CH₃), 2, 2.4 (m, 3H, CH₃), 3.9 (m, 2H, CH₂) 6.9 (s, 1H, CH), 7.1 (m, 1H, CH), 7.4 (m, 1H, CH), 7.5 (m, 1H, CH), 7.8 (m, 1H, CH), 8.1 (s, 1H, CH), 10 (m, 1H, CH) |
| 69 | 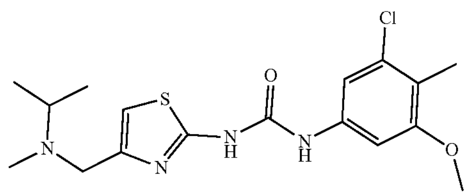 | 1-(3-chloro-5-methoxy-4-methylphenyl)-3-(4-((isopropyl(methyl)amino)methyl)thiazol-2-yl)urea | | | |

Example 5

3D STRUCTURE DETERMINATION AND EVALUATION OF LIGAND BINDING WITH NMR

The CAP-1 binding site, identified by NMR HSQC, is a superficial and shallow pocket in the apical region of capsid protein (CA). Mass spectrometry studies indicate that the apical region of capsid forms a capsid-capsid interface upon in vitro capsid assembly. It is generally believed that inhibitors of protein:protein interactions need to be fairly large and hydrophobic. However, CAP-1, a small organic molecule (MW 311.8) inhibits capsid:capsid interaction. Furthermore, mass action calculations show that ligand binding to as few as ~25 molecules of Gag per virion is sufficient to inhibit core assembly during viral maturation. Since it is postulated that CAP-1 binding induces a conformational change in capsid we have determined the 3D structure of CAP-1 bound capsid for use in structure based design of more potent ligands that bind to capsid protein apical cleft. Capsid protein ligands are also evaluated by NMR to determine their equilibrium dissociation constant from the capsid binding site.

Concentrated DMSO-d6 solutions of test compounds are prepared for NMR analysis. 2D $^1$H-$^{15}$N HSQC NMR spectra are obtained for aqueous solutions containing recombinant, $^{15}$N-labeled HIV-1 capsid protein and 10 microliters of added test compound. Data is obtained using a 600 MHz NMR instrument equipped with a cryoprobe. Samples that give rise to significantly perturbed NMR spectra are readily identified by visual or automated analysis of the NMR spectra (using NMR View software, One Moon Scientific, Inc.). Binding is indicated by perturbation relative to capsid protein alone ($^1H_N$ δδ>0.1 ppm; $^{15}$N δδ>0.5 ppm) of the chemical shifts of the following residues: Glu29, Lys30, Ala31, Phe32, Ser33, Glu35, Val36, Val59, Gly60, Gly61, His62, Gln63, Ala65, Met144 and Tyr145, all located at or near the apex of a helical bundle (helices 1, 2, 3, 4 and 7).

Equilibrium dissociation constants are calculated from 2D NMR data of selected capsid ligands. Representative $^1$H-$^{15}$N HSQC NMR data obtained upon titration of the capsid with CAP-1 are shown in FIG. 1. Although most signals were unaffected by the titrations, a subset of signals shifted as a function of increasing CAP-1 concentration, indicating site-specific binding. The chemical shift changes of perturbed by test compound binding are fit to 1:1 binding isotherms. CAP-1 affords an equilibrium dissociation constant ($K_D$) of 0.82±0.18 mM at 35° C., FIG. 3.

Example 6

CELL VIABILITY AND VIROLOGIC REPLICATION ASSAYS

Virology studies are performed to assess the antiviral potency of HIV-1 capsid ligands identified by NMR HSQC binding studies. The antiviral effect of these compounds is evaluated by parallel studies of inhibition of viral replication and cell viability. Viruses and cells for use in these assays may be obtained from the NIH AIDS Reagent Program.

6a. Determination of Antiviral Effect and Assessment of Cytotoxicity

Ligands of HIV-1 capsid identified by NMR HSQC studies are tested in an in vitro cytoprotection assay. The cytoprotection assay utilizes a laboratory-adapted RF strain of HIV-1 and CEM-SS cells or the NL4/3 (Accession number M19921) strain of HIV-1 and MT4 cells (catalog # 120 from the NIH AIDS Reagent Program).

CEM-SS Cells are well mixed and counted, and resuspended in RPMI 1640 media with 10% heat inactivated Fetal Bovine Serum 2 mm L-glutamine, 100 U/ml penicillin, 100 μg/ml streptomycin, and 10 μg/ml gentamycin. Serial or half-serial dilutions of test compound in RPTI 1640 are prepared (5 dilutions for a typical 6-point curve). 100 μl test compound or control compound, such as 0.01 μM AZT, are pipetted into test wells of a 96-well plate. 50 μl CEM-SS cells and 50 μl virus of known MOI are added to each compound-containing well. Reagent background wells containing only media and negative control wells containing 100 μl RPMI 1640 media, and 50 μl virus are also prepared.

Plates are incubated at 37° C. in a humidified $CO_2$ incubator for six days. Following incubation of the HIV-1 infected cells with the compound. Typically half log dilutions of compound, at concentrations from 100 μM to 0.3 μM, are used for a 6 point cell viability curve. Cytotoxicity of the compound is determined in parallel by measurement of the viability of mock-infected cells treated with the compound. Uninfected cells without compounds are used for a 100% viability control. Infected cells to which no compound is added provide a value for 100% of cell death due to viral infection. The number of surviving or viable cells is quantified by a tetrazolium-based colorimetric method using the CellTiter96® reagent (Promega, Madison, Wis.).

6b. Inhibition of Early Phase Virus Replication:

The effect of compounds on the early phase virus replication, from virus particle attachment through early gene, Tat expression, are evaluated using a CD4-positive LTR-β-galatosidase-expressing HeLa (MAGI) cell indicator line. This assay, described previously to assess the level of β-gal expression, has been modified and adopted in our laboratory. β-gal levels are quantified by photon detection assay, with virus infected cells that are not treated with a capsid formation inhibitor giving the highest level of expression. Effective capsid formation inhibitors reduce β-gal expression by 50% or more in the concentration range tested, and in many instances by more than 90%.

MAGI Cells are trypsinized and counted using the trypan blue exclusion method, and resuspended at a pre-determined concentration (usually 2×104 cells/well) in 10% FBS complete RPMI 1640. Cells are incubated 37° C. overnight.

The viruses are diluted to a pre-determined MOI/well, typically 0.01 to 1, in Pre-MAGI media plus 20 μg/well DEAE-dextran.

The assay plates are set up as follows.

Each drug is tested at 6 doses and in triplicate. Typically half log dilutions of compound, at concentrations from 100 μM to 0.3 μM, are used for a 6 point curve.

Each plate includes the following control wells:

Virus control, virus and 20 ug/mL Dextran Sulfate, in a total of 200 uL Pre-MAGI media plus 20 ug/mL DEAE-dextran;

Cell control, cells in 200 uL Pre-MAGI media plus 20 ug/mL DEAE-dextran without drug or virus; and Positive control, cells in 100 uL/well Pre-MAGI media plus 20 ug/mL DEAE-dextran, 50 μL prepared/diluted virus, and 50 μL of a compound of known activity.

Wells containing test compound are prepared by removing media from the cells and replacing with 100 uL/well Pre-MAGI media plus 20 ug/mL DEAE-dextran. 50 uL of 4× concentration test compound is added to each well. Add 50 uL of prepared/diluted virus is added per well. The plate(s) are incubated at 37° C. for 48 hours.

Following the 48 hour incubation period, the Gal-Screen Reagents are removed from 4° C. and allowed to warm to room temperature before using. Once the reagents have reached room temperature, the Gal-Screen Substrate is diluted 1:25 with Gal-Screen Buffer A or B (40 uL for every 960 uL).

100 μL of supernatant from all wells including Test Compound Wells, Cell Controls, Virus Controls and Positive Controls is removed and discarded. 100 uL of the Gal-Screen Reagent (Applied Biosystems, Foster City, Calif.) is added per well.

Plates are incubated at room temperature (25° C.) for 60–90 minutes or until constant light emission is reached. Plate(s) are read in a luminometer and measured for 0.1–1.0 sec/well.

What is claimed is:

1. A compound having the formula

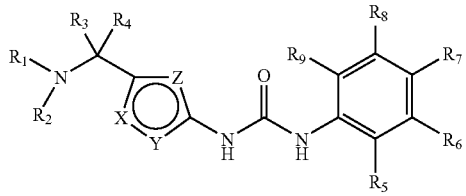

or a pharmaceutically acceptable salt thereof, wherein:
X, Y, and Z are each independently N, S, or CR', wherein at least one of X, Y, and Z is N or S; or
Each R' is independently hydrogen, halogen, hydroxy, $C_1$–$C_4$alkyl, $C_2$–$C_4$alkenyl, $C_2$–$C_4$alkynyl, $C_1$–$C_4$alkoxy, mono- or di-($C_1$–$C_4$alkyl)amino, $C_2$–$C_4$alkanoyl, $C_2$–$C_4$alkoxycarbonyl, $C_1$–$C_2$haloalkyl, or $C_1$–$C_2$haloalkoxy; or
$R_1$ is hydrogen, or
$R_1$ is $C_1$–$C_6$alkyl, $C_2$–$C_6$alkenyl, $C_2$–$C_6$alkenyl, ($C_3$–$C_7$cycloalkyl) $C_0$–$C_2$alkyl, or (phenyl)$C_0$–$C_2$alkyl, each of which is substituted with 0 to 3 substituents independently chosen from halogen, hydroxy, cyano, amino, nitro, oxo, —(C=O)$NH_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy; or
$R_2$ is hydrogen, or
$R_2$ is $C_1$–$C_6$alkyl, $C_2$–$C_6$alkenyl, $C_2$–$C_6$alkenyl, ($C_3$–$C_7$cycloalkyl) $C_0$–$C_2$alkyl, or (phenyl)$C_0$–$C_2$alkyl, each of which is substituted with 0 to 3 substituents independently chosen from halogen, hydroxy, cyano, amino, nitro, oxo, —(C=O)$NH_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy;
or $R_1$ and $R_2$ are taken together to form a 5-membered monocyclic heterocycle, which heterocycle is saturated, partially unsaturated, or aromatic, and is substituted with 0 to 3 substituents independently chosen from halogen, hydroxy, cyano, amino, nitro, oxo, —(C=O)$NH_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy; or
$R_3$ and $R_4$ are independently hydrogen, halogen, hydroxy, $C_1$–$C_4$alkyl, $C_1$–$C_4$alkoxy, mono- or di-($C_1$–$C_4$alkyl)amino, $C_1$–$C_2$haloalkyl, or $C_1$–$C_2$haloalkoxy;

$R_5$ is hydrogen, halogen, hydroxy, cyano, amino, straight chain $C_1$–$C_4$alkyl, straight chain $C_1$–$C_4$alkoxy, mono- or di-($C_1$–$C_4$alkyl)amino, $C_1$–$C_2$haloalkyl, or $C_1$–$C_2$haloalkoxy; or
$R_5$ is joined with $R_6$ to form a phenyl ring or a 5-membered heteroaryl ring having from 1 to 3 heteroatoms independently chosen from N, O, and S, where each ring is substituted with 0 to 3 substituents independently chosen from halogen, hydroxy, cyano, amino, nitro, —(C=O)$NH_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy;
$R_6$ and $R_7$ are independently
(i) hydrogen, halogen, hydroxy, cyano, amino, or nitro; or
(ii) $C_1$–$C_6$alkyl, $C_2$–$C_6$alkenyl, $C_2$–$C_6$alkynyl, $C_1$–$C_6$alkoxy, $C_2$–$C_6$alkanoyl, ($C_3$–$C_7$cycloalkyl) $C_0$–$C_2$alkyl, (phenyl)$C_0$–$C_2$alkyl, mono- or di-($C_1$–$C_6$alkyl)amino, $C_1$–$C_2$haloalkyl, or $C_1$–$C_2$haloalkoxy; each of which is substituted with $_0$ to $_3$ substituents independently chosen from halogen, hydroxy, cyano, amino, nitro, oxo, —(C=O)$NH_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy; or
(iii) a 5 membered heteroaryl group containing 1 or 2 heteroatoms independently chosen from N, S, and O; or
$R_6$ is joined with $R_5$; or
$R_6$ and $R_7$ are joined to form a phenyl ring or a 5-membered heteroaryl ring having 1 or 2 heteroatoms independently chosen from N, O, and S, where each ring is substituted with 0 to 3 substituents independently chosen from halogen, hydroxy, cyano, amino, nitro, —(C=O)$NH_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy; and
$R_8$ and $R_9$ are independently hydrogen, halogen, hydroxy, cyano, amino, straight chain $C_1$–$C_4$alkyl, straight chain $C_1$–$C_4$alkoxy, mono- or di-($C_1$–$C_4$alkyl)amino, $C_1$–$C_2$haloalkyl, or $C_1$–$C_2$haloalkoxy.

2. A compound or salt of claim 1 of the formula:

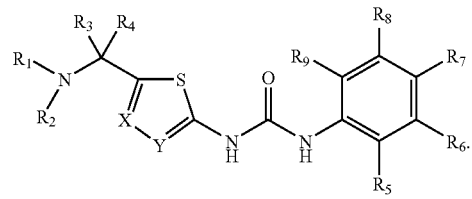

3. A compound or salt of claim 1 of the formula

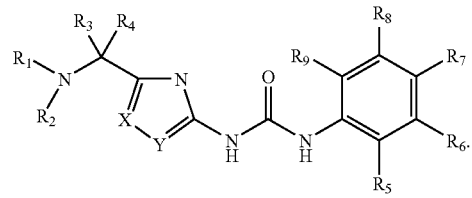

4. A compound or salt of claim 3 of the formula

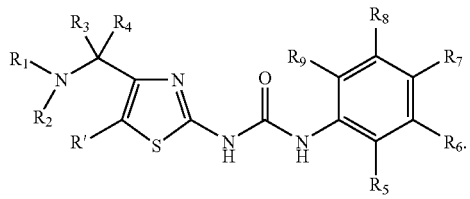

5. A compound or salt of claim 1 wherein
Each R' is independently hydrogen, halogen, hydroxy, $C_1$–$C_4$alkyl, $C_2$–$C_4$alkenyl, $C_2$–$C_1$–$C_4$alkoxy, mono- or di-($C_1$–$C_4$alkyl)amino, $C_2$–$C_4$alkanoyl, $C_2$–$C_4$alkoxycarbonyl, $C_1$–$C_2$haloalkyl, or $C_1$–$C_2$haloalkoxy.

6. A compound or salt of claim 5 wherein is hydrogen.

7. A compound or salt of claim 1 wherein
$R_1$ and $R_2$ are independently
hydrogen, or
$C_1$–$C_6$alkyl, $C_2$–$C_6$alkenyl, $C_2$–$C_6$alkynyl, ($C_3$–$C_7$cycloalkyl)$C_0$–$C_2$alkyl, or (phenyl)$C_0$–$C_2$alkyl, each of which is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

8. A compound or salt of claim 1 wherein
$R_1$ and $R_2$ are taken together to form a 5-membered monocyclic heterocycle, which heterocycle is saturated, partially unsaturated, or aromatic, and is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

9. A compound or salt of claim 1 wherein $R_3$ and $R_4$ are independently hydrogen or methyl.

10. A compound or salt of claim 1 wherein $R_5$, $R_8$, and $R_9$ are independently hydrogen, halogen, methyl, ethyl, methoxy, ethoxy, trifluoromethyl, or trifluoromethoxy.

11. A compound or salt of claim 10 wherein $R_5$, $R_8$, and $R_9$ are all hydrogen.

12. A compound or salt of claim 10 wherein
$R_6$ and $R_7$ are independently
(i) hydrogen, halogen, hydroxy, cyano, amino, or nitro; or
(ii) $C_1$–$C_6$alkyl, $C_2$–$C_6$alkenyl, $C_2$–$C_6$alkynyl, $C_1$–$C_6$alkoxy, $C_2$–$C_4$alkanoyl, ($C_3$–$C_7$cycloalkyl)$C_0$–$C_2$alkyl, (phenyl)$C_0$–$C_2$alkyl, mono- or di-($C_1$–$C_6$alkyl)amino, $C_1$–$C_2$haloalkyl, or $C_1$–$C_2$haloalkoxy each of which is substituted with 0 to 3 substituents independently chosen from halogen, hydroxy, cyano, amino, nitro, oxo, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

13. A compound or salt of claim 12 wherein $R_6$ and $R_7$ are independently hydrogen, halogen, cyano, methyl, methoxy, propynyl, or trifluoromethyl.

14. A compound or salt of claim 1, wherein
$R_1$ is joined with $R_6$ to form a phenyl ring or a 5-heteroaryl ring having from 1 to 3 heteroatoms independently chosen from N, O, and S, where each ring is substituted with 0 to 3 substituents independently chosen from halogen, hydroxy, cyano, amino, nitro, —(C=O)NH$_2$, $C_1$–$C_4$alkyl, $C_1$–$C_4$alkoxy, $C_2$–$C_4$alkanoyl, mono- and di-($C_1$–$C_4$alkyl)amino, $C_1$–$C_2$haloalkoxy.

15. A compound or salt of claim 1 wherein
$R_6$ and $R_7$ are joined to form a phenyl ring or a 5-membered heteroaryl ring having 1 or 2 heteroatoms independently chosen from N, O, and S, where each ring is substituted with 0 to 3 substituents independently chosen from halogen, hydroxy, cyano, amino, nitro, —(C=O)NH$_2$, $C_1$–$C_4$alkyl, $C_2$–$C_4$alkoxy, $C_2$–$C_4$alkanoyl, mono- and di-($C_1$–$C_4$alkyl)amino, $C_1$–$C_2$haloalkyl, and $C_1$–$C_2$haloalkoxy.

16. A compound or salt of claim 1, wherein the compound is 1-(3-chloro-4-methylphenyl)-3-(4-((isopropyl(methyl) amino)methyl)thiazol-2-Yl)urea;
1-(4-((isopropyl(methyl)amino)methyl) thiazol-2-yl)-3-p-tolylurea trifluoroacetic acid;
1-(4-((allyl(methyl)amino)methyl)thiazol-2-yl)-3-(3-chloro-4-methylphenyl)urea trifluoroacetic acid;
1-(3-chloro-4-methylphenyl)-3-(4-((dimethylamino)methyl)thiazol-2-yl)urea;
1-(3-chloro-4-methylphenyl)-3-(4-((dimethylamino)methyl)thiazol-2-yl)urea;
1-(4-((benzyl(methyl)amino)methyl)thiazol-2-yl)-3-(3-chloro-4-methylphenyl)urea;
1-(3-chloro-4-methylphenyl)-3-(4-(((2-methoxyethyl) (methyl)amino)methyl)thiazol-2-yl)urea;
1-(4-(((2-amino-2-oxoethyl)(methyl)amino)methyl)thiazol-2-yl)-3-(3-chloro-4-methylphenyl) urea;
1-(3-chloro-4-methylphenyl)-3-(4-((isobutyl(methyl) amino)methyl)thiazol-2-yl)urea;
1-(3-chloro-4-methylphenyl)-3-(4-((isopentyl(methyl) amino)methyl)thiazol-2-yl)urea;
1-(3-fluoro-4-methylphenyl)-3-(4-((isopropyl(methyl) amino)methyl)thiazol-2-yl)urea;
1-(3-bromo-4-methylphenyl)-3-(4-((isopropyl(methyl) amino)methyl)thiazol-2-yl)urea;
1-(3-iodo-4-methylphenyl)-3-(4-((isopropyl(methyl) amino)methyl)thiazol-2-yl)urea;
1-(3,4-dimethylphenyl)-3-(4-((isopropyl(methyl)amino) methyl)thiazol-2-yl)urea;
1-(4-((isopropyl(methyl)amino)methyl)thiazol-2-yl)-3-(4-methyl-3-(trifluoromethyl)phenyl)urea;
1-(3-chloro-4-cyanophenyl)-3-(4-((isopropyl(methyl) amino)methyl)thiazol-2-yl)urea;
1-(1H-indol-5-yl)-3-(4-((isopropyl(methyl)amino)methyl)thiazol-2-yl)urea;
1-(4-((isopropyl(methyl)amino)methyl)thiazol-2-yl)-3-(2-methylbenzo[d]thiazol-5-yl)urea;
1-(3-chlorophenyl)-3-(4-((isopropyl(methyl)amino)methyl)thiazol-2-yl)urea;
1-(3-bromophenyl)-3-(4-((isopropyl(methyl)amino)methyl)thiazol-2-yl)urea;
1-(4-((isopropyl(methyl)amino)methyl)thiazol-2-yl)-3-(naphthalen-2-yl)urea;
1-(3-chloro-4-methylphenyl)-3-(4-((isopropylamino)methyl)thiazol-2-yl)urea;
1-(4-fluoro-3-(trifluoromethyl)phenyl)-3-(4-((isopropyl (methyl)amino)methyl)thiazol-2-yl)urea;
1-(4-chloro-3-(trifluoromethyl)phenyl)-3-(4-((isopropyl (methyl)amino)methyl)thiazol-2-yl)urea;
1-(4-cyano-3-(trifluoromethyl)phenyl)-3-(4-((isopropyl (methyl)amino)methyl)thiazol-2-yl)urea;
1-(4-methoxy-3-(trifluoromethyl)phenyl)-3-(4-((isopropyl(methyl)amino)methyl)thiazol-2-yl)urea;

1-(3-(trifluoromethyl)phenyl)-3-(4-((isopropyl(methyl)amino)methyl)thiazol-2-yl)urea;

1-(4-(trifluoromethyl)phenyl)-3-(4-((isopropyl(methyl)amino)methyl)thiazol-2-Yl)urea;

1-(4-((cyclobutyl(methyl)amino)methyl)thiazol-2-yl)-3-(4-methyl-3-(trifluaromethyl)phenyl) urea;

1-(4-((cyclopropyl(methyl)amino)methyl)thiazol-2-yl)-3-(4-methyl-3-(trifluoromethyl)phenyl)urea;

1-(4-((sec-butyl(methyl)amino)methyl)thiazol-2-yl)-3-4-methyl-3-(trifluoromethyl)phenyl)urea;

1-(3-(3-hydroxyprop-1-ynyl)-4-methylphenyl)-3-(4-((isopropyl(methyl)amino) methyl)thiazol-2-yl)urea;

1-(4-((isopropyl(methyl)amino)methyl)thiazol-2-yl)-3-(4-methyl-3-(prop-1 -ynyl)phenyl)urea;

1-(3-(but-1-ynyl)-4-methylphenyl)-3-(4-((isopropyl(methyl)amino)methyl)thiazol -2-yl)urea;

1-(benzo[c][1, 2, 5]oxadiazol-4-yl)-3-(4-((isopropyl(methyl)amino)methyl)thiazol-2-yl)urea;

1-(benzo[c][1 ,2, 5]thiadiazol-4-yl)-3-(4-((isopropyl(methyl)amino)methyl)thiazol-2-yl)urea;

1-(4-((isopropyl(methyl)amino)methyl)thiazol-2-yl)-3-(2-methoxy-4-methylphenyl)urea;

1-(4-chloro-2-methoxyphenyl)-3-(4-((isopropyl(methyl)amino)methyl)thiazol-2-yl)urea;

1-(3-chloro-4-methylphenyl)-3-(4-(pyrrolidin-1-ylmethyl)thiazol-2-yl)urea;

1-(3-acetylphenyl)-3-(4-((isopropyl(methyl)amino)methyl)thiazol-2-yl)urea;

1-(3chloro-4-hydroxyphenyl)-3-(4-((isopropyl(methyl)amino)methyl)thiazol-2-yl)urea;

1-(3-chloro-4-(hydroxymethyl)phenyl)-3-(4-((isopropyl(methyl)amino)methyl) thiazol-2-yl)urea;

1-(3-chloro2-methoxyphenyl)-3-(4-((isopropyl(methyl)amino)methyl)thiazol-2-yl)urea;

1-(5-chloro-2-hydroxy-4-methylphenyl)-3-(4-((isopropyl(methyl)amino)methyl) thiazol-2-yl)urea;

1-(3-chloro-4-methylphenyl)-3-(6-((isopropyl(methyl)amino)methyl)pyridin-2-yl)urea;

1-(3-cyclopropyl-4-methylphenyl)-3-(4-((isopropyl(methyl)amino)methyl)thiazol-2-yl)urea;

1-(3-chloro-5-cyclopropylphenyl)-3-(4-((isopropyl(methyl)amino)methyl)thiazol-2-yl)urea;

1-(3-cyclopropylphenyl)-3-(4-((isopropyl(methyl)amino)methyl)thiazol-2-yl)urea;

1-(3-(furan-3-yl)-4-methylphenyl)-3-(4-((isopropyl(methyl)amino)methyl)thiazol-2-yl)urea;

1-(3-chloro-5-(furan-3-yl)phenyl)-3-(4-((isopropyl(methyl)amino)methyl)thiazol-2-yl)urea;

1-(3-(furan-3-yl)phenyl)-3-(4-((isopropyl (methyl)amino)methyl)thiazol-2-yl)urea;

1-(4-((isopropyl(methyl)amino)methyl) thiazol-2-yl)-3-(3-methoxy-5-(trifluoromethyl)phenyl)urea;

1-(3-chloro-4-(furan-3-yl)phenyl)-3-(4-((isopropyl(methyl)amino)methyl)thiazol-2-yl)urea; and 1-(3-chloro-5-methoxy-4-methylphenyl)-3-(4-((isapropyl (methyl)amino)methyl) thiazol-2-yl)urea.

17. A pharmaceutical composition, comprising a compound or salt of claim 1, in combination with at least one pharmaceutically acceptable carrier or excipient.

18. The pharmaceutical composition of claim 17, wherein the composition is formulated as an injectable fluid, an aerosol, a cream, an oral liquid, a tablet, a gel, a pill, a capsule, a syrup, or a transdermal patch.

19. A method of treating human patient infected with HIV-1 comprising administering a therapeutically effective amount of a compound of salt of claim 1 to the patient.

20. A compound or salt of claim 4 wherein

R' is hydrogen;

$R_1$ and $R_2$ are independently hydrogen, or $C_1$–$C_6$alkyl, $C_2$–$C_6$alkenyl, $C_2$–$C_6$alkynyl, $(C_3$–$C_7$cycloalkyl)$C_0$–$C_2$alkyl, or (phenyl)$C_0$–$C_2$alkyl, each of which is substituted with $_0$ to $_3$ substituents independently chosen from halogen, hydroxy, cyano, amino, nitro, oxo, —(C═O)NH$_2$, $C_1$–$C_4$alkyl, $C_1$–$C_4$alkoxy, $C_2$–$C_4$alkanoyl, mono- and di-($C_1$–$C_4$alkyl)amino $C_1$–$C_2$haloalkyl, and $C_1$–$C_2$haloalkoxy; and $R_3$ and $R_4$ are independently hydrogen or methyl.

* * * * *